United States Patent
Reiman

(10) Patent No.: US 9,492,114 B2
(45) Date of Patent: Nov. 15, 2016

(54) ACCELERATED EVALUATION OF TREATMENTS TO PREVENT CLINICAL ONSET OF ALZHEIMER'S DISEASE

(71) Applicant: Banner Health Systems, Inc., Phoenix, AZ (US)

(72) Inventor: Eric M. Reiman, Scottsdale, AZ (US)

(73) Assignee: Banner Health Systems, Inc., Phoenix, AZ (US)

( * ) Notice: Subject to any disclaimer, the term of this patent is extended or adjusted under 35 U.S.C. 154(b) by 0 days.

(21) Appl. No.: 14/510,049

(22) Filed: Oct. 8, 2014

(65) Prior Publication Data

US 2015/0080703 A1  Mar. 19, 2015

Related U.S. Application Data

(63) Continuation-in-part of application No. 11/155,711, filed on Jun. 17, 2005, now abandoned.

(60) Provisional application No. 60/580,762, filed on Jun. 18, 2004, provisional application No. 61/888,389, filed on Oct. 8, 2013.

(51) Int. Cl.
*A61B 5/00* (2006.01)
*A61B 5/05* (2006.01)
(Continued)

(52) U.S. Cl.
CPC ........... *A61B 5/4848* (2013.01); *A61B 5/0035* (2013.01); *A61B 5/0476* (2013.01);
(Continued)

(58) Field of Classification Search
CPC .... A61B 5/0035; A61B 5/0476; A61B 5/05; A61B 5/055; A61B 5/4088; A61B 5/4848; A61B 6/032; A61B 6/037; G01N 2800/2821; G01N 33/5088; G01N 33/6896; G06F 19/3443
See application file for complete search history.

(56) References Cited

U.S. PATENT DOCUMENTS

| 5,617,861 A | 4/1997 | Ross et al. |
| 6,377,833 B1 | 4/2002 | Albert |

(Continued)

FOREIGN PATENT DOCUMENTS

| WO | WO 2006/009887 | 1/2006 |
| WO | WO 2006/041816 | 4/2006 |

OTHER PUBLICATIONS

U.S. Appl. No. 11/242,820; Office Action mailed Apr. 9, 2015.
(Continued)

*Primary Examiner* — Michael Rozanski
(74) *Attorney, Agent, or Firm* — Lewis Roca Rothgerber Christie LLP

(57) ABSTRACT

Systems and methods for evaluating prospective treatments for progressive brain disorders like Alzheimer's disease and the progressive effects of aging involve the use of an imaging device communicatively coupled to a computing device. The imaging device may takes a plurality of brain imaging measurements from each of a plurality of human subjects who are divided into a treated group and an untreated group based on various subject data including whether the subjects carry certain alleles of genes known to increase the risk of developing the brain disorder at issue. The computing device receives the brain imaging measurements from the imaging device and applies an advanced processing method that permits enhanced computational efficiency when calculating rates of change for the two groups and determining whether any calculated difference between the rates is statistically significant.

15 Claims, 4 Drawing Sheets

(51) Int. Cl.
A61B 5/0476 (2006.01)
A61B 6/03 (2006.01)
A61B 5/055 (2006.01)
G01N 33/50 (2006.01)
G01N 33/68 (2006.01)
G06F 19/00 (2011.01)

(52) U.S. Cl.
CPC .............. *A61B 5/05* (2013.01); *A61B 5/055* (2013.01); *A61B 5/4088* (2013.01); *A61B 6/032* (2013.01); *A61B 6/037* (2013.01); *G01N 33/5088* (2013.01); *G01N 33/6896* (2013.01); *G06F 19/3443* (2013.01); *G01N 2800/2821* (2013.01)

(56) References Cited

U.S. PATENT DOCUMENTS

| | | | |
|---|---|---|---|
| 6,560,354 | B1 | 5/2003 | Maurer et al. |
| 6,917,845 | B2 | 7/2005 | Hsiung et al. |
| 7,239,908 | B1 | 7/2007 | Alexander et al. |
| 2002/0113787 | A1 | 8/2002 | Ray et al. |
| 2003/0092980 | A1 | 5/2003 | Nitz |
| 2003/0225717 | A1 | 12/2003 | Keefer et al. |
| 2004/0066956 | A1 | 4/2004 | Ashton |
| 2004/0126892 | A1 | 7/2004 | Bogomolov |
| 2005/0014997 | A1 | 1/2005 | Ruchti |
| 2005/0078869 | A1 | 4/2005 | Pelletier et al. |
| 2005/0080330 | A1 | 4/2005 | Masuzawa et al. |
| 2005/0084145 | A1 | 4/2005 | Pelletier et al. |
| 2005/0207631 | A1 | 9/2005 | Martens et al. |
| 2005/0209785 | A1 | 9/2005 | Wells et al. |
| 2005/0283054 | A1 | 12/2005 | Reiman |
| 2006/0074290 | A1 | 4/2006 | Chen |

OTHER PUBLICATIONS

Abdi, Herve, "Partial Lease Squares (PLS) Regression," In: Encyclopedia for research methods for the social sciences (Lewis-Beck M et al., eds) (2003), Thousand Oaks (CA): Sage.
Alexander et al., "Longitudinal PET Evaluation of Cerebral Metabolic Decline in Dementia: A Potential Outcome Measure in Alzheimer's Disease Treatment Studies", Am J. Psychiatry 2002; 159:738-745.
Alexander, G.E., et al., "Application of the scaled subprofile model to functional imaging in neuropsychiatric disorders: A principle component approach to modeling brain function in disease," Human Brain Mapping 2:79-94(1994).
Alexander, GE., APOE e4 dose effect on gray matter atrophy in cognitively normal adults, Society for Neuroscience, 2003.
Alexander, GE. et al., "Evaluation of gray matter atrophy in cognitively normal apoe E e-4 homozygotes and heterozygotes with voxel-based MRI morphometry," 1st Annual meeting of Society for Neuroscience.
Alexander, GE., Individual differences in attentional performance predict verbal learning in healthy elderly, Arizona Alzheimer's Research Consortium, 2005.
Alexander, GE., Interactive effects of APOE e4and physical fitness on gray matter in cognitively normal adults, Society for Neuroscience, 2004.
Alexander, GE., Neuroimaging, The Dementias: Diagnosis, Treatment, and Research, 3rd Edition, 2003, pp. 103-136.
Alexander, GE., Regional network analysis of gray matter atrophy in healthy aging, Abstract presented at the annual meeting of the International Neuropsychological Society, Baltimore, MD, 2004.
Alexander, GE., Regional network of magnetic resonance imaging gray matter volume in healthy aging. NeuroReport 17, Jul. 2006, pp. 951-956.
Alexander, GE., Regional network pattern of MRI gray matter volume in Alzheimer's dementia, Alzheimer's & Dementia, The Journal of the Alzheimer's Association, vol. 2, Issue 3, 2006, S665.

Alexander GE, Chen K, Reiman EM., Abnormalities in gray matter density in young adults at genetic risk for late-onset Alzheimer's disease. Presented at the 8th Internat Conf on AD and Related Dis, Stockholm, Jun. 2002 [abstract].
American Psychiatric Association. Diagnostic and statistical manual of mental disorders. 4th ed. Washington, DC: American Psychiatric Association, 1994.
Anderson, N.D., et al., "The effects of divided attention on encoding and retrieval-related brain activity: A PET study of younger and older adults," J.Cogn Neurosci,12:775-792, Massachusetts Institute of Technology (2000).
Archibald, R., Improving tissue segmentation of human brain MRI through preprocessing by the Gegenbauer reconstruction method, NeuroImage 20, 2003, pp. 489-502.
Arfanakis, K., et al., "Combining independent component analysis and correlation analysis to probe interregional connectivity in fMRI task activation datasets," Magn Reson.Imaging 18:921-930 (2000).
Ashburner, J., et al., "Multimodal image coregistration and partitioning—a unified framework,"Neuroimage. 6:209-217 (1997).
Ashburner, J, Friston KJ., Voxel-based morphometry—the methods. Neuroimage 2000; 11:805-821.
Baxter, LC, Apolipoprotein E e4 affects new learning in cognitively normal individuals at risk for Alzheimer's disease, Neurobiol. Aging 24, 2003, pp. 947-952.
Beckmann, C.F., et al., "Probabilistic independent component analysis for functional magnetic resonance imaging," IEEE Trans. Med.Imaging 23:137-152, Feb. 2004.
Bierer LM, Haroutunian V, Gabriel S, Neocortical Neuofibrillary tangles correlate with dementia severity in Alzheimer's disease. Arch. Neurol. 1995;52:81-88.
Bobinski, Maciek., "MRI of entorhinal cortex in mild Alzheimer's disease", The Lancet, Jan. 2, 1999, vol. 353, p. 38-40.
Bokde, A., Discrimination between Alzheimer's disease patients and healthy subjects: Resting FDG-PET data, International Conference on Alz. Dis. Related Disord., Madrid, Spain, 2006.
Borga, Magnus, et al.,"A unified approach to PCA, PLS, MLR, and CCA," Report LiTH-ISY-R-1992,ISY,SE-581 83 (1997).
Cagnin A. Brook DJ, Kennedy AM, In-vivo measurement of activated microgilia in dementia. Lancet. 2001;358:461-7.
Calhoun, V.D., et al., "Latency (in)sensitive ICA, Group independent component analysis of fMRI data in the temporal frequency domain," Neuroimage. 20:1661-1669 (2003).
Calhoun, V.D., et al., "Spatial and temporal independent component analysis of functional MRI data containing a pair of task-related waveforms," Hum.Brain Mapp. 13:43-53 (2000).
Caselli, RJ., A distinctive interaction between chronic anxiety and problem solving in asymptomatic APOE e4 homozygotes, The Journal of Neuropyschiatry and Clinical Neurosciences 16, 2004, pp. 320-329.
Caselli, RJ., Alzheimer's disease: A century later, J. Clin Psychiatry 67, 2006. pp. 1784-1800.
Caselli, RJ. A preliminary fluorodeoxyglucose positron emission tomography study in healthy adults reporting dream-enactment behavior, Sleep 29, 2006, pp. 927-933.
Caselli, RJ., Brain imaging and cognitive studies of asymptomatic APOE e4 carriers, International Neuropsychological Society Abst., 2003.
Caselli, RJ., Changes in personality during mid-life may correlate with risk for Alzheimer's disease, NeuroBiology of Aging 25, No. S2, 2004, p. 112.
Caselli, RJ., Cognitive domain decline in healthy apolipoprotein E e4 homozygotes before the diagnosis of mild cognitive impairment, Arch Neurol 64, 2007, pp. 1306-1311.
Caselli, RJ., Longitudinal changes in cognition and behavior in asymptomatic carriers of the APOE e4 allele, Neurology 62, 2004, pp. 1990-1995.
Caselli, RJ., Longitudinal Neuropsychological and behavioral study of presymptomatic ApoE e4 carriers and noncarriers, Annual meeting of the American Acad. Of Neurology, 2003.
Caselli, RJ., Presymptomatic longitudinal decline in frontally mediated cognitive skills and memory in cognitively normal late middle aged APOE e4 carriers, Alzheimer's and Dementia 2, 2006, S292.

(56) References Cited

OTHER PUBLICATIONS

Caselli, RJ., The degenerative dementias, Textbook of Clincal Neurology, 2nd Edition, 2003, pp. 681-711.
Caselli, RJ., Therapeutic Interventions: Drug treatments and other therapies, In: Radin L, Radin G, editors. What if its not Alzheimer's? 2nd edition. Amherst: Prometheus Books, 2007, pp. 73-89.
Chau, W., et al., "Multi-modality imaging data analysis with partial least squares, Brain and Cognition," 54:140-142, (2004).
Chen, H., et al., "A method based on independent component analysis for processing fMRI data," Sheng Wu Yi. Xue.Gong.Cheng Xue. Za Zhi. 19:64-66, Jan. 19, 2002.
Chen, K., Accounting for multiple comparisons using concurrences of the presence of activation and absence of deactivation in neuroimaging studies, Human Brian Mapping, Annual Meeting, 2003.
Chen, K., A monte-carlo simulation package for the calculation of statistical power, familywise type I error of various global indices associated with neuroimaging studies, Society of Nuclear Medicine 51st Annual Meeting, 2004. 9th International Conference of Azheimer's Dis Related Disord. 2004.
Chen, K., A monte-carlo simulation package, multiple comparison corrections and power estimation incorporating secondary supportive evidence, Proceedings of Complex Medical Engineering, IEEE, 2007, pp. 913-191.
Chen, K., An automated algorithm for the computation of brain volume change from sequential MRIs using an iterative principle component analysis and its evaluation for the assessment of the whole-brain atrophy rates in patients with probable Alzheimer's disease, NeuroImage, May 2004, vol. 22, No. 1, pp. 134-143.
Chen, K., An automated, normative-based fluorodeoxyglucose positron emission tomography image-analysis procedure to aid Alzheimer's disease diagnosis using statistical parametric mapping and interactive image display, Acad. Molecular Imaging Annual Conference, 2005.
Chen, K., Characterization of the image-derived carotid artery input function using independent component analysis for the quantitation of [18F] fluorodeoxyglucose positron emission tomography images, Phys. Med. Biol. 52, 2007, pp. 7055-7071.
Chen, K., Correlations between apolipoprotein E e4 gene dose and whole brain atrophy rates, AM J. Psychaitry, 2007, pp. 916-921.
Chen, K., Detection of gray matter atrophy from sequential MRI in AD patients, World Congress of Medical Physics and Biomedical engineering, 2003.
Chen, K., Estimation of whole-brain atrophy accounting for increased variability due to MRI scanner changes in our longitudinal neuroimaging Alzheimer's risk study, Soc. For Neurosci., 2006.
Chen, K., Gray tissue segmentation and voxel based morphometry in detecting gray matter atrophy from successive MRI: a preliminary study, Neuroimage 14, 2001, pp. 1238-1243.
Chen, K. et al., Inter-frame co registration of dynamically acquired fluoro-deoxyglucose positron emission tomography human brain data, Proceedings of Complex Medical Engineering, IEEE, 2007, pp. 907-912.
Chen, K., et al., "Linking Functional and Structural Brain Images with Multivariate Network Analysis: Description and Preliminary Application Using the Partial Least Square Method," World Congress on Medical Physics and Biomedical Engineering, Sydney, (2003).
Chen, K., Monte-carlo based neuroimaging set-level multiple-comparison correction, J Int. Federation of Automated Control Conf., 2003.
Chen, K., et al., "Noninvasive quantification of the cerebral metabolic rate for glucose using positron emission tomography, 18F-fluoro-2deoxyglucose, the Patlak method, and an image-derived input function," J.Cereb.Blood Flow Metab 18:716-723, (1998).
Chen, K., The noninvasive quantification of FDG PET using the input function derived over an automatically defined carotid artery region, Society for Neuroscience, 2004.
Chen, K., The pattern and serverity of FDG PET abnormalities in Alzheimer's disease and amnestic mild cognitive impairment: Preliminary findings from the Alzheimer's disease neuroimaging initiative, internat. Conf. AD Prevention, Washington, DC, 2007.
Chen K, Reiman EM, Alexander GE. Automated method using interactive principle component analysis for detecting brain atrophy rates from sequential MRI in persons with Alzheimer's disease, Soc Neurosci Abstr, 2001 [abstract].
Chen K, Reiman EM, He J,. Evaluation of an interactive principal component analysis for detecting whole brain volume change in small animal magnetic resonance imaging. Presented at the 8th Internat Conf on AD and related Dis, Stockholm, 2002 [abstract].
Chen K, Reiman EM, Alexander GE. Using Partial-Least Squares to Demonstrate a Correlation between Combined PET/MRI Scores and Apolipoprotein E e4 Gene Dose. Imaging Consortium IC-P-101: Posters, pp. S672-S673.
Chen K, Reiman Em, Alexander GE., Whole brain atrophy rates in cognitively normal persons at genetic risk for Alzheimer's disease. Presented at the 8th Internat Conf on AD and Related Dis, Stockholm, Jun. 2002 [abstract].
Chen, K., Six-month cerebral metabolic declines in Alzheimer's disease, amenestic mild cognitive impairment and elderly normal control groups: Preliminary findings from the Alzheimer's disease neuroimaging initiative, Internat. Conf. AD Prevention, Washington, DC, 2007.
Coffey CE, Wilkinson WE, Parashos IA. Quantitative cerebral anatomy of the aging human brain: a cross-sectional study using magnetic resonance imaging. Neurology 1992; 42:527-36.
Cohen D, Eisdorfer C. Depression in family members caring for a relative with Alzheimer's Disease. J Am Geriatr Soc 1988;36:885-889.
Coon, KD., A High-density whole-genome association study reveals that APOE is the major susceptibility gene for sporadic late-onset Alzheimer's disease, J Clinic Psychiatry 68, 2007, pp. 613-618.
Coon, KD., A novel resequencing technique allows quantitation of heteroplasmy in MTDNA sequence vairants found in AD patients, Alzheimer's and Dementia 2, 2006, S199.
Coon, KD., Peripheral mitochondrial DNA defects and enzyme functions as a mechanism for Alzheimer's disease, Neurobiol. Aging 25, S497, 2004.
Coon, KD., Preliminary demonstration of an allelic association of the IREB2 gene with Alzheimer's disease, Journal of Alzheimer's Disease 9, 2006, pp. 225-233.
Coon, KD et al., Quantitation of Heteroplasmy of mtDNA sequence variants identified in a population of AD patients and controls by array-based resequencing, Mitochondrion 6, 2006, pp. 194-210.
Convit A, de Leon MJ, Tarshish C., Hippocampal Volume losses in minamally impaired elderly. Lancet 1995;345:266.
Convit A, de Leon MJ, Tarshish C., Specific hippocampal volume reduction in individuals at risk for Alzheimer's disease. Neurobiol Aging 1997;18:131-8.
Corder EH, Jelic V, Basun H., No difference in cerebral glucose metabolism in patients with Alzheimer disease and differing apolipoprotein E genotypes. Arch Neurol 1997;54:273-7.
Corder EH, Saunders AM, Strittmatter WJ, et al. Gene dose of apolipoprotein E type 2 allele for late onset alzheimers disease. Nature Genetics 1994;7:180-184.
Corder EH, Saunders AM, Risch NJ., Protective effect of apolipoprotein E type 2 allele for late onset Alzheimer disease. Nature Genetics 1994; 7:180-184.
Csernansky JG, Wang L, Joshi S., Early DAT is distinguished from aging by high-dimensional mapping of the the hippocampus.Dementia of the Alzheimer type. Neurology 200 Dec. 12;55(11):1636-43.
Davis, DA., Voxel-based network analysis of regional glucose metabolism in Alzheimer's disease, Society for Neuroscience, 2006.
DeCarli, C., et al., "Lack of age-related differnces in temporal lobe volume of very healthy adults," AJNR Am.J.Neuroradiol. 15:689-696, (1994).
de Leon MJ, Ferris SH, George AE. Computed tomography and positron emission transaxial evaluations of normal aging and Alzheimer's disease. J Cereb Blood Flow Metab 1983;3:391-394.
de Leon MJ, George AE, Stylopoulos LA, Smith G, Miller DC. Early marker for Alzheimer's disease: the atrophic hippocampus. Lancet 1989;672-673.

(56) References Cited

OTHER PUBLICATIONS de Leon MJ, Golomb J, George AE. The radiologic prediction of Alzheimer's disease: the atrophic hippocampal formation. Am J Neuroradiol 1993;14:897-906.
Demaerschalk, BM., Dementia treatment: let the evidence lead us, Evidence-Based Neurological Management, Candelise L, Editor, Blackwell Publishing, 2007, pp. 184-198.
Deweer B., Lehericy S, Pillon B., Memory disorders in probably alzheimer's disease; the role of hippocampal atrophy as shown in MRI, J.Nuerol Neurosurg Pshychiatry, 1995:58:590-597.
Div Neuropharmacological Drug Products, US Food and Drug Administration. Background Document for Joint Advisory Committee Meeting of Nov. 18, 2002: Issues Related to the Role of Brain Imaging as an Outcome Measure in Phase Trials of Putative Drugs for Alzheimer's Disease. 2002[Memo].
Duan, J.R., et al., "Single-trial veriability in event-related BOLD signals," Neuroimage. 15:823-835, (2002).
Duara R, Grady CL, Haxby JV, et al. Positron emission Tomography in Alzheimer's disease. Neurology 1986;36:879-887.
Du, AT, Schuff N, Zhu XP, et al. Atrophy rates of entorhinal cortex in AD and normal aging. Neurology 2003; 60: 481-6.
Du At, Schuff N, Kramer JH. Higher atrophy rate of entorhinal cortex than hippocampus in Alheimer's disease. Neurology 2003. (in press).
Du AT, Schuff N, Amend D, Lasskso MP, Hsu YY, Jagust WJ. Magnetic resonance imaging of the entorhinal cortex and hippocampus in mild cognitive impairment and Alzheimer's disease. J Neurol Pshychiatry 2001;71:441-447.
Dunckley, T., Gene expression correlates of neurofibrillary tangles in Alzheimer's disease, Neurobiology of Aging 27, 2006, pp. 1359-1371.
Dunckley, T., Mechanism of Neurofibrillary tangle-induced neuronal degeneration leading to AD, NeuroBiology of Aging 25, S2, 2004, p. 427.
Esbensen, K., et al., "Fermentation monitoring using multi-sensor systems: feasibility study of the electronic tongue," Anal.Bioanal. Chem. 378:391-395 (2003).
Esposito, F., et al., "Real-time independent component analysis of fMRI time-series," Neuroimage. 20:2209-2224 (2003).
Etnier, JL., ApoE-4 genotype and aerobic fitness as predictors of cognitive performance by older woman, Arizona Alzheimer's Research Consortium, 2004.
Etnier, JL., Cognitive performance in older woman relative to ApoE-e4 genotype and aerobic fitness, Medicine & Science in Sports & Exercise 39, 2007, pp. 199-207.
Etnier, JL., The differential benefits of aerobic fitness for cognitive performance as a function of ApoE genotype, Medicine & Science in Sports & Exercise 37, 2005, S462-S463.
Evans, DA, Funkenstein HH, Albert MS. Prevalence of Alzheimer's disease in a community population of older persons: higher than previously reported: JAMA 1989;262:2551-2556.
Farrer LA, Cupples LA, Haines JL, Hyman B, Kukull WA, Mayeux R, Myers RH, Pericak-Vance MA, Risch N, van Duijn CM. Effects of age, sex, and ethnicity on the association between apolipoprotein E genotype and Alzheimer disease. A meta-analysis. APOE and Alzheimer Disease Meta Analysis Consortium. JAMA 1997;278(16):1349-56.
Fleming TR, DeMets DL. Surrogate end points in clinical trials: are we being misled? Ann Intern Med 1996;125:605-613.
Foster NL, Chast TN, Fedio P. Alzheimer's disease: Focal cortical changes shown by positron emission tomography. Neurology 1983;33:961-965.
Fox NC, Warrington EK, Stevens JM. Atrophy of the hippocampal formation in early familial Alzheimer's disease. A longitudinal MRI study of at-risk members of a family of a family with a amyloid precursor protein 717Val-Glymutation. Ann NY Acad Sci 1996;777:226-32.
Fox NC, Freeborough PA. Brain Atrophy progression measured from registered serial MRI. J Magn Reson Imaging 1997;7:1069-1075.
Fox NC, Crum WR, Scahill RI. Imaging of onset and progression of Alzheimer's disease with voxel-compression mapping of serial magnetic resonance images. Lancet 2001;358:201-205.
Fox NC, Warrington EK, Freeborough PA. Presymptomatic hippocampal atrophy in Alzheimer's disease: a longitudinal MRI study. Brain 1996;119:2001-2007.
Fox NC, Freeborough PA, Rossner MN. Visualization and quantification of rates of atrophy in Alzheimer's disease. Lancet 1996;348:94-97.
Fox NC, Cousens S, Scahill R. Using serial registered brain magnetic resonance imaging to measure disease progression in Alzheimer disease: power calculations and estimates of sample size to detect treatment effects. Arch Neurol 2000:57:333-444.
Freebourough PA, Fox NC. The boundary shift integral: an accurate and robust measure of cerebral volume changes from registered repeat MRI. IEEE Trans Med Imaging 1997;16:623-629.
Frisoni GB, Lasskso MP, Beltramello A. Hippocampal and entorhinal cortex atrophy in frontotemporal dementia and Alzheimer's disease. Neurology 199;52:91-100.
Friston, K.J., "Dynamic causal modelling," Neuroimage. 19:1273-1302 (2003).
Friston, Karl J., Functional and Effective connectively in Neuroimaging: A Synthesis, Human Brain Mapping. 1994, vol. 2:56-78.
Games D, Adams D, Alessandrini R. Alzheimer-type neuropathology in transgenic mice overexpressing V717F amyloid precursor protein. Nature 1995;373:523-527.
Gerkin, R., A person's reported history of hypothyroidism is related to apolipoprotein E e4 gene dose, NeuroBiology of Aging 25, S2, 2004, p. 511.
Gerlach, R.W., et al., "Partial least-squares path modeling with latent variables," Anal.Chim.Acta 112:417-421 (1979).
Golomb, J., et al., "Hippocampal formation size in normal human aging: a correlate of delayed secondary memory performance," Learn.Mem. 1:45-54, May-Jun. 1994.
Golomb J, de Leon MJ, Kluger A. Hippocampal atrophy in normal aging-an association with recent memory impairment. Arch Neurol 1993;50:967-973.
Golub G, Van Loan C (1989) Matrix Computations, Baltimore, The Johns Hopkins University Press.
Good, C.D., et al., "A voxel-based morphometric study of ageing in 465 normal adult human brains. Neuroimage," 14:21-36, May 11, 2001.
Gonzalez-Lima F, Berndt JD, Valla J, Games D, Reiman EM. Reduced corpus callosum, fornix and hippocampus in PDAPP transgenic mouse model of Alzheimer's disease. NeuroReport 2001;12:2375-2379.
Guo, H., An input function estimation method for FDG-PET human brain studies, Nuci, Med. Biol. 34, 2007, pp. 483-492.
Guo, H., Clustering huge data sets for parametric PET imaging, BioSystems 71, 2003, pp. 81-92.
Habib, R., et al., "Memory encoding and hippocampally-based novelty/familiarity discrimination networks," Neuropsychologia 41:271-279 (2003).
Hammers, A., et al., "Implementation and application of a brain template for multiple volumes of interest," Hum.Brain Mapp. 15:165-174 (2001).
Hanson, KD., Relation of regional MRI white matter reductions to gray matter in Alzheimer's disease, Society for Neuroscience, 2006.
Hauss-Wegrzyniak B, Chen K, Galons JP. Detecting an experimentally induced reduction in mouse brain volume using sequential high-resolution MRI's and the iterative PCA method. Presented at the 8th Internat Conf on AD and Related Dis, Stockholm, 2002 [abstract].
Haxby JV, Grady CL, Koss E., Longitudinal study of cereral metabolic asymmetries and associated neuropsychological patterns in early dementia of the Alzheimer type. Arch Neurol 1990;47:753-760.
He, T., The computation of mannitol-induced changes in mouse brain volume using sequential MRI and an iterative principal component analysis, NeuroBiology of Aging 25, S2, 2004, p. 283.

(56) References Cited

OTHER PUBLICATIONS

Higuchi M, Arai H, Nakagawa T. Regional cerebral glucose utilization is modulated by the dosage of apolipoprotein E type 4 allele and alpha 1-antichymotrypsin type A allele in Alzheimer's disease. Neuroreport 1997;8:8639-43.

Hirono N, Mori E, Yasuda M. Lack of association of apolipoprotein E epsilon 4 allele dose with cerebral glucose metabolism in Alzheimer disease. Alzheimer Dis Assoc Disord 1998;12:362-7.

Hoegaerts, L., et al., "Kernel PLS variants for regression," Proc.of the 11th European Symposium on Artificial Neural Networks 203-208, Apr. 23-25, 2003.

Hoffman JM, Welsh-Bohmer KA, Hanson M. FDG PET imaging in patients with pathologically verified dementia. J Nuci Med 2000;41:1920-1928.

Holcomb L., Gordon MN, McGowan E, et al. Accelerated Alzheimer-type phenotype in transgenic mice carrying both mutant amyloid precursor protein and presenilin 1 transgenes. Nature Med 1998;4:97-100.

Horwitz B., "Functional Interactions in the Brain: Use of Correlations Between Regional Metabolic Rates," Journal of Cerebral Blood Flow and Metabolism 11:A114-A120 (1991).

Horwitz, B., et al., "Network analysis of PET-mapped visual pathways in Alzheimer type dementia," Neuroreport 6:2287-2292, Nov. 27, 1995.

Horwitz, B., et al., "Neural modeling, functional brain imaging, and cognition," Trends Cogn Sci, 3:91-98, Mar. 1999.

Hoskuldsson, A., "PLS Regression and the Covariance," Chemometrics http://www.acc.umu.se/~tnkjtg/Chemometrics/Editorial, Jul. 2004.

Hsiao K, Chapman P, Nilsen S. et al., Correlative memory deficits, AB elevation, and amyloid plaques in transgenic mice. Science 1996; 274-99-102.

Huentalman, M., Calmodulin-binding transcription activator 1 (CAMTA1) alleles predispose human episodic memory performance, Human Molecular Genetics 16, 2007, pp. 1469-1477.

Hwang, D., et al., "Inverse modeling using multi-block PLS to determine the environmental conditions that provide optimal cellular function," Bioinformatics. 20:487-499 (2004).

Hyvarinen, A., et al., "Independent Component Analysis," New York, John Wiley & Sons, Inc. (2001).

Ibanez, V., et al., "Regional glucose metabolic abnormalities are not the results of atrophy in Alzheimers Disease," Neurology 50:1585-1593, Jun. 1998.

Ibanez, V., Resting state brain glucose metabolism is not reduced in normotensive healthy men during aging, after correction for brain atrophy, Brain Research Bulletin 63, 2004, pp. 147-154.

Iidaka, T., et al., "The effect of divided attention on encoding and retrieval in episodic memory revealed by positron emission tomography," J. Cogn Neurosci. 12:267-280(2000).

Jack CR, Petersen RC, O'Brien PC, Tangalos EG. MR-based hippocampal volumetry in the diagnosis of Alzheimer's disease. Neurology 1992;42:183-188.

Jack CR Jr, Petersen RC, O'Brien PC, Xu Y, et al., Rate of Medial temporal lobe atrophy in typical aging and Alzheimer's disease. Neurology 1998; 51:993-9.

Jack Cr Jr, Petersen RC, O'Brien PC, Xu Y, et al., Medial temporal atrophy on MRI in normal aging and very mild Alzheimer's disease. Neurology 1997;49:786-94.

Jack CR Jr., Petersen RC, O'Brien PC, Xu Y, O'Brien PC, Smith GE, Ivnik RJ, et al., Rates of hippocampal atrophy correlate with change in clinical status in aging and AD. Neurology 2000;55(4):484-489.

Jack CR Jr, Petersen RC, O'Brien PC, Xu Y, et al., Prediction of AD with MRI-based hippocampal volume in mild cognitive impairment. Neurology 1999;52:1397-1403.

Jagust, W.J. et al., Longitudinal studies of regional cerebral metabolism in Alzheimer's disease. Neurology, Jun. 1988,38:909-912.

Jernigan, T.L., et al., "Cerebral structure on MRI, Part I: Localization of age-related changes," Biol.Psychiatry 29:55-67 (1991).

Johnson, SC., Activation of brain regions vulnerable to Alzheimer's disease: The effect of mild cognitive impairment, Neurobiology of Aging 27, 2006, pp. 1604-1612.

Johnson, SC., Hippocampal adaptation to face repetition in healthy elderly and mild cognitive impairment, Neuropsychologia 42, 2004, pp. 980-989.

Juottonen K, Laakso MP, Insausti R. et al. Volumes of the entorhinal and perirhinal cortices in Alzheimer's diesease. Neurobiol Aging 1998;19:15-22.

Juottonen K, Laakso MP, Partanen K, et al. Comparative MR analysis of the entorhinal cortex and hippocampus in diagnosing Alzheimer's disease. AJNR Am J Neuroradiol 1999;20:139-44.

Katzman R, Kawas C. The epidemiology of dementia and Alzheimer's disease. In: Terry RD, Katzman R, and Bick KL, eds. Alzheimer Disease. New York: Raven Press, 1994;105-122.

Kaye JA, Swihart T, Howieson D, et al. Volume loss of the hippocampus and temporal lobe in the healthy elderly person destined to develop dementia. Neurology 1997;48:1297-304.

Keightly, M.L., et al., "An fMRI study investingating cognitive modulation of brain regions associated with emotional processing of visual stimuli," Neuropsychologia 41:585-596 (2003).

Kessiak J, Nalcioglu O, Cotman C., Quantification of magnetic resonance scans for hippocampal and parahippocampal atrophy in Alzheimer's disease. Neurology 1991;41:51-54.

Khachaturian, Z S., The five-five, ten-ten plan for Alzheimer's disease (editorial). Neurobiol Aging 1992;197-198.

Khalil, Z. et al., "Sensory peptides as neuromodulators of wound healing in aged rats." J. Gerontol. Series A: Bio. Sci. and Med. Sci. 1996, vol. 51, No. 5, pp. B354-B361.

Khodr, B. Effect of short-term and long-term antioxidant therapy on primary and secondary ageing neurovascular processes. J. Gerontol. Series A: Biol. Sci. and Med. Sci. 2003, vol. 58, pp. B698-B708.

Kiebal, S.J., et al., "MRI and PET coregistration—a cross validation of statistical parametric mapping and automated image registration," Neuroimage. 5:271-279 (1997).

Killiany R, Moss M, Albert M, Tamas S., Temporal lobe regions on magnetic resonance imaging identify patients with early Alzheimer's disease. Arch Neurol 1993;50:949-954.

Killiany RJ, Gomez-Isla T, Moss M, et al., Use of structural magnetic resonance imaging to predict who will get Alzheimer's Disease. Ann Neurol 200;47:430-439.

Klunk, W.E., et al., "Imaging brain amyloid in Alzheimers disease with pittsburgh Compound-B," Ann.Neurol.55:305-319 (2004).

Krasuski JS, Alexander GE, Horwitz B, et al., Volumes of medial temporal lobe structure in patients with Alzheimer's disease and mild cognitive impairment (and in healthy controls). Biol Psychiatry 1998;43:60-9.

Kuhl DE, Koeppe RA, Minoshima S, et al., In vivo mapping of cerebral acetylcholinesterase activity in aging and Alzheimer's disease. Neurology. 1999;52:691-9.

Kuhl DE, Metter EJ, Riege WH, Phelps ME., Effects of human aging on patterns of local cerebral glucose utilization determined by the 18F-fluorodeoxyglucose method. J Cereb Blood Flow Metab 1982;2:163-71.

Laakso M, Partanen K, Riekkinen P, et al., Hippocampal volumes in Alzheimer's disease, Parkinson's disease with and without dementia, and in vascular dementia: an MRI study. Neurology 1996;46:678-681.

Laakso MP, Soininen H, Partanen K, et al., Volumes of hippocampus, amygdala and frontal lobes in the MRI-based diagnoses of early Alzheimer's disease: correlation with memory functions. J Neural Transm Park Dis Dement Sect 1995;9:73-86.

Lehericy S, Baulac M, Chiras J, et al., Amygdalohippocampal MR volume measurements in the early states of Alzheimer disease. AM Jneuroradiol 1994;15:927-937.

Lee, P.C. et al., "Impaired wound healing and angiogenesis in eNOS-deficient mice" Am. J. Physiol. Heart Circ. Physiol. 1999, vol. 277, pp. 1600-1608.

Leow, AD., For the ADNI preparatory phase study: Longitudinal stability of MRI for mapping brain change using tensor-based morphometry, Neuroimage 31, 2006, pp. 627-640.

(56) References Cited

OTHER PUBLICATIONS

Liang WS, Dunckley T, Beach TG. Gene expression profiles in anatomically and functionally distinct regions of the normal aged human brain. Physiol Genomics 25:311-322.2007.
Lin, F.H., et al., "Multivariate analysis of neuronal interactions in the generalized partial least squares frame work: simulations and empirical studies," Neuroimage. 20:625-642 (2003).
Lin, L., MRI template and atlas toolbox for the C57BL/6J Mouse Brain, IEEE EMBS Special Topic Conference on Neural Engineering, Arlington, Virginia, Mar. 16-19, 2005.
Lin, L., Template based region of interest strategies for measuring ventricular volume in mouse brain MR images: Empirical validation with pharmiceutical-induced ventricular increase, NeuroBiology of Aging 25, S2, 2004, p. 267.
Lobaugh, N.J., et al., "Spatiotemporal analysis of experimental differences in event-related potential data with partial least squares," Psychophysiology 38:517-530 (2001).
Loessner, A., et al., "Regional cerebral function determined by FDG-PET in healthy volunteers: normal patterns and changes with age," J.Nucl.Med. 36:1141-1149, Jul. 1995.
Lopes, J.A., et al., "Multiblock PLS analysis of an industrial phamaceutical process," Biotechnol.Bioeng.80:419-427, Nov. 20, 2002.
Magistretti PJ and Pellerin L., Cellular bases of brain energy metabolism and their relevance to functional brain imaging: evidence for a prominen: role of astrocytes. Cereb Cortex 1996;6:50-61.
Mahley RW., Apolipoprotein E: Cholesterol transport protein with expanding role in cell biology. Science 1988; 240:622-30.
Mark RJ, Pang Z, Geddes JW, et al., Amyloid B-Peptide Impairs Glucose Transport in Hippocampal and Cortical Neurons: Involvement of Membrane Lipid Peroxidation, J Neurosci 1997;17:1046-54.
Mathis CA, Bacskai BJ, Kajdasz ST, et al., A lipophilic thioflavin-T derivative for positron emission tomography (PET) imaging of amyloid in brain. Biorg Med Chem Lett 2002;12:295-8.
McGeer EG, Peppard RP, McGeer PL, et al., 18 Fluorodeoxyglucose positron emission tomography studies in presumed Alzheimer cases, including 13 serial scans. Can J Neurol Sci 1990;17:1-11.
Mcintosh, A.R., "Mapping cognition to the brain through neural interactions," Memory. 7:523-548 (1999).
Mcintosh, A.R., et al., "Recruitment of unique neural systems to support visual memory in normal aging," Curr. Biol. 9:1275-1278 (1999).
Mcintosh, A.R., et al., "Spatial pattern analysis of functional brain images using partial least squares," Neuroimage. 3:143-157 (1996).
Mcintosh, A.R., et al., "Structural equation modeling and its application to network analysis in functional brain imaging," Human Brain Mapping 2-22 (1994).
Mcintosh, A.R., "Understanding neural interactions in learning and memory using functional neuroimaging," Ann.N.Y.Acad.Sci. 855:556-571 (1998).
McKeown, M.J., et al., "Analysis of fMRI data by blind separation into independent spatial comoponents," Hum. Brain Mapp. 6:160-188 (1998).
McKhann G, Drachman D, Folstein M, Katzman R, Price D, Stadlan EM, Clinical diagnosis of Alzheimer's disease: report of the NINCDS-ADRDA Work Group under the auspices of the Department of Health and Human Services Task Force on Alzheimer's Disease. Neurology 1984;34:939-944.
Mega MS, Chen SS, Thompson PM, et al., Mapping histology to metabolism: coregistration of stained whole-brain sections to premortem PET in Alzheimer's disease. Neuroimage 1997;5:147-153.
Meguro K, Blaizot X, Kondoh Y, et al., Neocortical and hippcampal glucose hypometabolism following neurotoxic lesions of the entorhinal and perirhinal cortices in the non-human primate as shown by PET. Implications for Alzheimer's disease. Brain 1999;122:1519-31.

Meltzer, C.C., et al., "Does cerebral blood flow decline in healthy aging? A PET study with partial-volume correction," J.Nucl. Med. 41:18842-1848, Nov. 2000.
Mielke R, Herholz K, Grond M., Clinical deterioration in probable Alzheimer's disease correlates with progressive metabolic impariment of association areas. Dementia 1994;5:36-41.
Mielke R, Zerres K, Uhlhaas S, et al., Apolipoprotein E polymorphism influences the cerebral metabolic pattern in Alzheimer's disease. Neurosci Lett 1998;254:49-52.
Minoshima, S., et al., "A diagnostic approach in Alzheimers disease using three-dimensional sterotactic surface projections of fluorine-18-FDG PET," J.Nucl.Med. 36:1238-1248 (1995).
Minoshima S, Foster NL, Kuhl DE., Posterior cingulate cortex in Alzheimer's disease. Lancet 1994;344-895.
Miyata M, Smith JC., Apolipoprotein E allele-specific antioxidant activity and effects on cytotoxicity by oxidative insults and bamyloid peptide. Nat Genet 1996;14:55-61.
Moeller, J.R., et al., "Scaled subprofile model: a statistical approach to the analysis of functional patterns in postiron emission tomographic data," J. Cereb.Blood Flow Metab 7:649-658 (1987).
Morris JC., Olichney JM, Thal LJ, et al., Cerebral amyloid deposition and diffuse plaques in "normal" aging: Evidence for presymptomatic and very mild Alzheimer's disease. Neurology 1996;46:707-719.
Morris JC., Role of biomarkers in studies of presymptomatic Alzheimer's disease, Alzheimer's & Dementia 1, 2005, pp. 145-151.
Morritz, C.H., et al., "Whole-brain functional MR imaging activation from a finger-tapping task examined with independent component analysis," AJNR AM.J.Neuroradiol. 21:1629-1635, Oct. 2000.
Murphy, D.G., et al., "Age-related differences in volumes of subcortical nuclei, brain mater, and cerebrospinal fluid in healthy men as measured with magnetic resonance imaging," Arch. Neurol. 49:839-845 (1992).
Nestor, P.G., et al., "A new statistical method for testing hypotheses of neuropsychiological/MRI relationships in schizophrenia: partial least squares analysis," Schizophr.Res.53:57-66 (2002).
O'Donnell, B.F., et al., "Idenfication of neural circuits underlying P300 abnormalities in schizophrenia," Psycophysiology 36:388-398 (1999).
Panza, F., Current epidemiology of mild cognitive impairment and other predementia syndromes, AM J. Geriatr Psychaitry 13, 2005, pp. 633-644.
Panza, F., Cognitive frailty: Predementia syndrome and vascular resk factors, Neurobiology of Aging 27, 2006, pp. 933-940.
Papassotiropoulos, A., Common KIBRA alleles are associated with human memory performance, Science 314, 2006. pp. 475-478.
Papassotiropoulos, A., Genetics, transcriptomics and proteomics of Alzheimer's disease, Journal Clinical Psychiatry 67, 2006, pp. 652-670.
Pearson, J., Huentleman MJ, Halperin RF. Identification of the genetic basis for complex disorders by use of pooling-based genome-wide single-nucleotide-polymorphism association studies, The American Journal of Genetics vol. 80, pp. 126-139, 2007.
Petersen RC, Smith GE, Waring SC, Ivnik, RJ, Tangalos EG, Kokmen E. Mild Cognitive impairment: Clinical Characterization and outcome. Arch Neurol. 1999;56:303-308.
Pierce, G.F. et al., "Pharmacologic enhancement of Wound Healing." Annu. Rev. Med. 1995, vol. 46, pp. 467-481.
Piert M, Koeppe RA, Girordani B, et al., Diminished glucose transport and phosphorylation in Alzheimer's disease determined by dynamic FDG-PET. J NucL Med 1996;37:201-8.
Rajah, M.N., et al., "Frontotemporal interactions in face encoding and recognition," Brain Res. Cogn. Brain Res. 8:259-269 (1999).
Rajah, M.N., et al., "Overlap in the functional neural systems involved in semantic and episodic memory retrieval," J.Cogn Neurosci. 17:470-482, Mar. 2005.
Reiman EM, Casseli RJ, Chen K, et al., Abnormalities in regional brain activity in young adults at genetic risk for late-onset Alzheimer's disease Presented at the 8th Internat Conf on AD and Related Dis, Stockholm, Jun. 2002 [abstract].
Reiman EM, Caselli RJ., Alzheimer's Disease. Maturitas 1993;31:185-200.

(56) References Cited

OTHER PUBLICATIONS

Reiman, EM., Brain Imaging and genomics in the study of cognitively normal persons at differential risk for Alzheimer's disease, Cold Springs Harbor Laboratory Neurodegenerative Diseases Meeting, 2006.
Reiman EM, Chen K, Caselli RJ. Cholesterol-Related Genetic Risk Scores are Associated with Hypometabolism in Alzheimer's-Affected Brain Regions. Neuroimage, Apr. 15, 2008; 40(3): 1214-1221.
Reiman, EM., Correlations between apolipoprotein E e4 gene dose and brain-imaging measurments of regional hypometabolism, Procedings of Natl Academy Sciences of the USA, vol. 102, No. 23 (Jun. 2005), pp. 8299-8302.
Reiman, EM., Correlations between cholesterol-related genetic risk scores and lower brain-imaging measurements of regional glucose metabolism, Sociology for Neuroscience, 2005.
Reiman, E.M., et al., "Declining brain activity in cognitively normal apolipoprotein E epsilon 4 heterozygotes: A foundation for using positron emission tomography to efficiently test treatments to prevent Alzheimer's disease," Proc.Natl Acad.Sci.U.S.A 98:3334-3339, Mar. 13, 2001.
Reiman EM, Caselli EM, Chen K, et al., Effects of age on cerebral glucose metabolism in APOE 4 carriers and noncarriers. Presented at the 8th Internat Conf on AD and Related Dis, Stockholm, Jun. 2002 [abstract].
Reiman, E.M., et al., "Functional brain abnormalities in young adults at genetic risk for late-onset Alzheimer's dementia," Proc. Natl.Acad.Sci.U.S.A. 101:284-289, Jan. 6, 2004.
Reiman, EM., FDG PET in cognitively normal persons at genetic risk for Alzheimer's dementia, Arizona Alzheimer's Consortium Annual Meeting, 2003.
Reiman EM, Uecker A, Caselli RJ, et al., Hippocampal volumes in cognitively normal persons at genetic risk for Alzheimer's disease. Ann Neurol 1998;44:288-291.
Reiman EM, Linking Brain Imaging and Genomics in the Study of Alzheimer's Disease and Aging. Ann. N.Y. Acad. Sci. 1097:94-113 (2007).
Reiman, EM., Neuroimaging in geriatric psychiatry, Comprehensive Textbook of Psychiatry, 8th Edition, 2005.
Reiman, EM., Neuroimaging in the study of amnestic mild cogntive impairment, ICAD, Madrid, 2006.
Reiman EM, Chen K, Alexander GE. PET Measurements of Posterior Cingulate Glucose metabolism are Superior to MRI Measurments of Hippocampal Volume in Distinguishing Cognitively Normal Persons of Differential Genetic Risk for Alzheimer's Disease. Oral O1-05-03:Early Detection and Diagnosis 2 p. S177.
Reiman EM., Positron emission tomography and magnetic resonance imaging in the study of cognitively normal persons at differential genetic risk for Alzheimer's dementia, The Living Brain and Alzheimer's Disease, 2004, pp. 151-177.
Reiman EM, Chen K, Alexander GE, Caselli RJ., Positron emission tomography studies of cognitively normal persons at genetic risk for Alzheimer's disease. Presented at the IPSEN Foundation Conference on the Living Brain and Alzheimer's Disease. Paris. 2003.
Reiman EM, Caselli RJ, Yun LS et al., Preclinical Evidence of Alzheimer's Disease in Persons Homozygous for the e4 Allele for Apolipoprotein E. N Engle J Med 1996:752-758.
Reiman EM, Proposition: Two Imaging Techniques are Better than One for the Evaluation of Putative Alzheimer's Disease-Slowing Treatments. Preconference—Imaging IM p. S94.
Reiman EM, Uecker A, Gonzalez-Lima F, Minear D., Chen K, Callaway N L, Berndt, JC, Games D., Tracking Alzheimer's disease in transgenic mice using fluorodeoxyglucose autoradiography. NeuroReport 2000;11:987-991.
Reiman EM, Caselli RJ, Alexander GE, Chen K., Tracking the decline in cerebral glucose metabolism in persons and laboratory animals at genetic risk for Alzheimer's disease. Clinical Neuroscience Research 2001;1:194-206.
Rusinek H, de Leon M, George A, et al., Alzheimer disease: measuring loss of cerebral gray matter with MR imaging. Radiology 1991;178:109-114.
Ryan, L., Neuroimaging: Overview of methods and application, Handbook of Physiological Research Methods in Health Physiological Research Methods in Healthy Psychology, L.J. Luecken and L.C. Gallo (Eds.), Thousand Oaks, California: Saga Press 2008, pp. 371-394.
Salmon, E., et al., "Decrease of frontal metabolism demonstrated by positron emission tomography in a population of healthy elderly volunteers," Acta Neurol.Belg. 91:288-295 (1991).
Saunders AM, Strittmatter WJ, Schmechel D, et al., Association of apolipoprotein E allele e4 with late-onset familial and sporadic Alzheimer's disease. Neurology 1993;43:1467-1472.
Saunders AM, Hulette C, Welsh-Bohmer KA, et al., Specificity, sensitivity, and predictive value of apolipoprotein-E genotyping for sporadic Alzheimer's disease. Lancet 1996; 348:90-93.
Scahill RI, Schott JM, Stevens JM, et al., Mapping the evolution of regional atrophy in Alzheimer's disease: unbiased analysis of fluid-registered serial MRI. Proc Natl Acad Sci USA 2002;99:4703-4707.
Schaffer, M. et al., "Neuropeptides." Arch. Surg. 1998, vol. 133, pp. 1107-1116.
Schmithorts, V.J., et al., "Comparison of three methods for generating group statistical inferences from independent component analysis of functional magnetic resonance imaging data," J.Magn Reson.Imaging 19:365-368 (2004).
Schott JM, Fox NC, Frost C, et al., Assessing the onset of structural change in Familial Alzheimer's disease. Ann Neurol 2003;53:181-188.
Schneider, LE., Metabolic mapping of glucose uptake I PSAPP mouse model of AD: Sensorimotor hyperarousal correlated with auditory amyloid pathology, Neurobiology Aging 25, 2004, S250.
Schuff N, Amend D, Ezekiel F, et al., Change of hippocampal N-acetyl aspartate and volume in Alzheimer's disease. Neurology 1997;49:1513-21.
Schwartz WI, Smith CB, Davidssen L, et al., Metabolic mapping of functional activity in the hypothalamic neurohypophysial system of the rat. Science 1979;205:723-725.
Seab, J, Jagust W, Wong S, et al., Quantative NMR measurements of hippocampal atrophy in Alzheimers disease. Magn Reson Med 1988;8:200-208.
Seshadri S, et al., Plasma homocysteine as a Risk Factor for Dementia and Alzheimer's Disease. New Engl J Med;346:476-483.
Shi, H.P. et al., "Supplemental dietary arginine enhances wound healing in normal but not inducible nitric oxide synthase knockout mice." Surgery, Aug. 2000. vol. 128, No. 2, pp. 374-378.
Shogi-Jadid K, Smal GW, Agdeppa ED, et al., Localization of neurofibrillary tangles (NFTs) and beta-amyloid plaques (Aps) in the brains of living patients with Alzheimer's disease. Am J Geriatr Pyschiatry 2002;10:24-35.
Silverman, D., et al., "Positron Emission Tomography in Evaluation of Dementia Regional Bain Metabolism and Long-term Outcome," JAMA 286:2120-2127, Nov. 7, 2001.
Small GW, Mazziotta JC, Collins MT, et al., Apolipoprotein E type 4 allele and cerebral glucose metabolism in relatives at risk for familial Alzheimer disease. J Am Med Assoc 1995;273:942-947.
Small, Gary., "Cerebral metabolic and cognitive decline in persons at genetic risk for Alzheimer's disease," Proceedings of the National Academy of Sciences of the United States of America, May 23, 2000, vol. 97, No. 11, pp. 6037-6042, PNAS, Washington D.C., (Catagory X document, the whole document, abstract, and p. 6037, col. 2, para 3, and p. 6041, col. 2, para 3, relevant to claims 1-23).
Smith, JF., Network analysis of single-subject fMRI during a finger opposition task, NeuroImage 32, 2006, pp. 325-332.
Smith, JF., Network analysis of single-subject fMRI during a finger tapping, Neuroscience, 2003.
Smith GS, de Leon MJ, George AE, et al., Topography of cross-sectional and longitudinal glucose metabolic deficits in Alzheimer's disease. Pathophysiologic implications. Arch Neurol 1992;49:1142-1150.

(56) References Cited

OTHER PUBLICATIONS

Snowdon DA, Tully CL, Smith CD, Riley KP, Markesbery WR., Serum folate and the severity of atrophy of the neocortex in Alzheimer disease: findings from the nun study. Am J Clin Nutr 2000;71:993-998.

Soininen H, Partanen, Pitkanen A, et al., Decreased hippocampal volume asymmetry on MRIs in nondemented elderly subjects carrying the apolipoprotein 4 allele. Neurology 1995;45:391-392.

Solfrizzi, V., Vascular risk factors, incidence of MCI, and rates of progression of dementia, Neurology 63, 2004, pp. 1882-1891.

Strittmatter WJ, Weisgraber KH, Huang DY, et al., Binding of human apolipoprotein E to synthetic amyloid B peptide isoform-specific effects and implications for late-onset Alzheimer disease. Proc Natl Acad Sci USA 1993;90:98-8102.

Strittmatter WJ, Weisgraber KH, Goedert M, et al., Hypothesis: microtubule instability and paired helical filament formation in the Alzheimer disease brain are related to apolipoprotein E genotype. Exp Neurol 1994;125:163-171.

Tang, Y., Introduction: Human Brain Function, Edition II, Frakwiak, RSJ, Friston, KJ, Frith, CD et al. (Eds)., Beijing: China Press, 2006, pp. 790-791.

Teipel, SJ., Age related cortical gray matter reductions in non-demented Down's syndrome adults determined by MRI with voxel-based morphometry, Brain 127, 2004, pp. 811-824.

Teipel, SJ., Cortical and sub-cortical changes in preclinical and clinical stages of Alzheimer's disease assessed with magnetic reasonance imaging, International Conference on Alz. Dis. Related Disord., Madrid, Spain, 2006.

Teipel, SJ., Regional pattern of hippocampus and corpus callosum atrophy in Alzheimer's disease in relation to dementia severity: Evidence for early neocortical degeneration, Neurobiol Aging 24, 2003, pp. 85-94.

Teipel, SJ., Relation of corpus callosum and hippocampal size to age in nondemented adults with downs syndrome, American Journal of Psychiatry 160, 2003, pp. 1870-1878.

Temple R., A regulatory authority's opinion about surrogate endpoints. In: Nimmo WS, Tucker GT, eds. Clinical Mearsurement in Druge Evaluation. New York, NY: John Wiley & Sons, Ltd; 1995:3-22.

Terry RD, DeTeresa R, Hansen LA., Neocortical cells counts in normal human adult aging. Ann Neurol 1987;21:530-9.

Terry RD, Maskiah E, Hansen LA., The Neuropathology of Alzheimer Disease and the Structural Basis of its Cognitive Altercations. In: Terry RD, Katzman R, Bick KL, and Sisodia SS, eds. Alzheimer Disease 2nd Ed. Philadelphia: Lippincott Williams & Wilkins 1999; 187-206.

Terry RD, DeTeresa R, Hansen LA., Physical basis of cognitive alterations of Alzheimer's disease: synapse loss is the major correlate of cognitive impairment. Ann Neurol 1991;30:572-580.

Thal, L., The role of biomarkers in clinical trials for Alzheimer disease, Alzheimer Dis Assoc Disord 20, 2006. pp. 6-15.

Thompson PM, Mega MS, Woods RP, et al., Cortical change in Alzheimer's Disease detected with a disease-specific population-bassed brain atlas. Cereb Cortex 2001;11:1-16.

Valla J, Chen K, Berndt JD, et al., Effects of image resolution on autoradiographic measurements of posterior cingulate activity in PDAPP mice: Implications for functional brain imaging studies in transgenic mouse models of Alzheimer's disease. NeuroImage 2002;16:1-6.

Valla J, Berndt JD, Gonzalez-Lima F., Energy hypometabolism in posterior cingulate cortex of Alzheimer's patients: superficial Laminar Cytochrome oxidase associated with disease duration. J Neurosci. 2001;21:4923-30.

Valla, J., Impaired platelet mitchrondrial activity in Alzheimer's disease and mild cognitive impariment, Mitchondrion 6, 2006, pp. 323-330.

Valla, J., Metabolic mapping of cytochrome oxidase activity demonstrates abnormalities in learning/memory circuits in PSAPP double-transgenic mice, Neurobiol. Aging 25, 2005, S246.

Valla, J., No evidence of significant white matter disruption in the TG2576 mouse model of Alzheimer's disease: Implications for in vivo microimaging. Presented at the 8th Internat Conf on AD and Related Dis, Stockholm, Jun. 2002 [absstract].

Valla, J., Nonprogressive transgene-related callosal and hippocampal changes in PDAPP mice, NeuroReport 17, 2006, pp. 829-832.

Visser Pj, Scheltens P, Verhey FR, et al., Medial temporal lobe atrophy and memory dysfunction as predictors for dementia in subjects with mild cognitive impairment. J Neurol 1999;246:477-85.

Webster, JA., Sorl1 as an Alzheimer's disease predisposition gene?, Neuro-dengenerative Diseases, 2007, pp. 1-5.

Westerhuis, J.A., et al., "Deflation in multiblock PLS," Journal of Chemometrics 15:485-493 (2001).

Westerhuis, J.A., et al., "Multivariate modelling of the tablet manufacturing process with we granulation for tablet optimization and in-process control," Int.J.Pharmaceut. 156:109-117 (1997).

Westerhuis, J.A., et al., "Optimisation of the composition and production of mannitol/microcrystalline cellulose tablets. Int.J. Pharmeceut," 143:151-162 (1996).

Wheeler-Rice, L., Individual differences in attentional performance predict verbal learning in healthy elderly, Society for Neuroscience, 2005.

Wisniewski T, Castano EM, Golabek A, et al., Acceleration of Alzheimer's Fibril formation by apolipoprotein E in vitro. Am J Pathol 1994;145:1030-1035.

Worsley, K.J., et al., "Characterizing the response of PET and fMRI data using multivariate linear models," Neuroimage. 6:305-319 (1997).

Wu, X., A variant of logistic transfer function in Infomax and a postprocessing procedure for independent component analysis applied for fMRI data, Magn. Reason. Med., 2007, pp. 703-711.

Young, A.A. et al., Dose response characteristics for the hyperglycemic, hyperlactemic, hypotensive and hypocalcemic actions of amylin and calcitonin gene-related peptide-I (CGRP alpha) in the fasted, anesthetized rat. Life Sci. 1993, vol. 52, No. 21, pp. 1717-1726.

Xu Y, Jack CR Jr, O'Brien PC, et al., Usefulness of MRI measures of entorhinal cortex versus hippocampus in AD. Neurology, 2000;54:1760-7.

European Application No. 05 77 2647, Search Report dated Apr. 14, 2008, 5 pages.

PCT Application No. PCT/US2005/021557, International Search Report and Written Opinion mailed Sep. 18, 2006.

PCT Application No. PCT/US2005/035608, International Search Report and Written Opinion mailed Nov. 22, 2006.

China Application No. 200580041489.6; Office Action dated Apr. 8, 2011.

China Application No. 200580041489.6; Office Action dated Mar. 1, 2010.

U.S. Appl. No. 11/155,711; Office Action mailed Jun. 19, 2014.

U.S. Appl. No. 11/155,711; Final Office Action mailed Jan. 15, 2014.

U.S. Appl. No. 11/155,711; Office Action mailed Aug. 5, 2013.

U.S. Appl. No. 11/155,711; Final Office Action mailed Aug. 4, 2011.

U.S. Appl. No. 11/155,711; Office Action mailed Dec. 7, 2010.

U.S. Appl. No. 11/155,711; Final Office Action mailed Mar. 19, 2010.

U.S. Appl. No. 11/155,711; Office Action mailed Jul. 2, 2009.

U.S. Appl. No. 11/242,820; Final Office Action mailed Jun. 5, 2014.

U.S. Appl. No. 11/242,820; Office Action mailed Nov. 6, 2013.

U.S. Appl. No. 11/242,820; Final Office Action mailed Jun. 19, 2013.

U.S. Appl. No. 11/242,820; Office Action mailed Jan. 22, 2013.

U.S. Appl. No. 11/242,820; Final Office Action mailed Mar. 20, 2012.

U.S. Appl. No. 11/242,820; Office Action mailed Jul. 19, 2011.

U.S. Appl. No. 11/242,820; Final Office Action mailed Oct. 22, 2015.

ACCELERATED EVALUATION OF TREATMENTS TO PREVENT CLINICAL ONSET OF ALZHEIMER'S DISEASE

CROSS-REFERENCE TO RELATED APPLICATIONS

The present application is a continuation-in-part and claims the priority benefit of U.S. patent application Ser. No. 11/155,711 filed Jun. 17, 2005, which claims the priority benefit of U.S. provisional application No. 60/580,762 filed Jun. 18, 2004; the present application also claims the priority benefit of U.S. provisional patent application No. 61/888,389 filed Oct. 8, 2013, the disclosures of which are incorporated herein by reference.

BACKGROUND

1. Field of the Disclosure

The present disclosure relates to medical treatment evaluation systems and methods. More particularly, it concerns advanced evaluation systems and methods concerning prospective treatments for progressive brain disorders (both neurological and psychiatric) and the progressive effects of aging on the brain.

2. Description of the Related Art

Alzheimer's Disease

Alzheimer's disease (AD) is a rapidly growing public health problem. Clinically, AD is characterized by a gradual and progressive decline in memory and other cognitive functions, including language skills, the recognition of faces and objects, the performance of routine tasks, and executive functions. It is also frequently associated with other distressing and disabling behavioral problems. Histopathological features of AD include: neuritic and diffuse plaques (in which the major constituent is the β-amyloid protein), neurofibrillary tangles (in which the major constituent is the hyperphosphorylated form of the microtubule-associated protein τ), and the loss of neurons and synapses.

Aside from its debilitating effect on patients themselves, AD also places a terrible burden on their families. Tellingly, about half of all primary caregivers caring for AD patients become clinically depressed.

AD is a prevalent problem. According to one community survey, AD afflicts about 10% of those over the age of 65 and almost half of those over the age of 85. As the population grows older, the prevalence and cost of AD is expected to increase dramatically. By 2050, for example, the prevalence of AD in the United States is projected to quadruple from about 4 million cases to about 16 million cases—without accounting for any increase in a patient's life expectancy. Unsurprisingly, the cost of caring for patients is also estimated to quadruple from about 190 million to 750 million dollars per year—without any adjustment for inflation. Effective prevention therapies are urgently needed to avert what is becoming an overwhelming public health problem.

In recent years, scientific progress has raised the hope of identifying treatments that may halt the progression of AD or even prevent its onset altogether. This recent progress has included: the discovery of genetic mutations and at least one susceptibility gene that account for many cases of AD; the characterization of other AD risk factors and pathogenic molecular events that could be targeted by potential treatments; the development and use of improved research methods for identifying new therapeutic targets (e.g., in the fields of genomics and proteomics); the development of promising animal models (including transgenic mice containing one or more AD genes) that may help to clarify disease mechanisms and screen candidate treatments; suggestive evidence that several available interventions (e.g., estrogen-replacement therapy, anti-inflammatory medications, statins, which might be associated with a lower risk and later onset of AD; the discovery of medications which at least modestly attenuate AD symptoms (e.g., several acetylcholinesterase inhibitors and the N-methyl-D-aspartate [NMDA] inhibitor memantine); and the development of other potentially disease-modifying investigational treatments (e.g., anti-amyloid immunization and medication therapies, which inhibit the production, aggregation, and neurotoxic sequelae of Aβ and/or promote its clearance, drugs that inhibit the hyperphosphorylation of tau and drugs that protect neurons against oxidative, inflammatory, excitatory, and other potentially toxic events).

Problematic Subject Size, Study Durations, and Expense in Prevention Studies

Even if a prevention therapy is only modestly helpful, it could provide an extraordinary public health benefit. For instance, a therapy that delays the clinical onset of AD by only five years might reduce the number of cases by half. Unfortunately, however, determining whether or when cognitively normal persons treated with a candidate preclinical AD prevention therapy develop cognitive impairment and AD requires thousands of volunteers, many years, and great expense.

One way to reduce the samples and time required to assess the efficacy of an AD prevention therapy is to conduct a clinical trial in patients with mild cognitive impairment (MCI), who may have a 10-15% rate of conversion to probable AD and commonly have histopathological features of AD at autopsy. Randomized, placebo-controlled clinical trials in patients with MCI could thus help establish the efficacy of putative "early AD" therapies. Using clinical outcome measures, the only practical way to establish the efficacy of "preclinical AD therapies" (i.e., interventions started in cognitively unimpaired persons and intended to postpoine, reduce the risk, or completely prevent the clinical onset of AD) has been to restrict the randomized, placebo-controlled study to subjects in advanced age groups—a strategy which still requires extremely large samples, a study duration of several years, and significant cost.

While these strategies are likely to play significant roles in the identification of effective prevention therapies, it remains possible that subjects will require treatment at a younger age or at an even earlier stage of underlying disease for a candidate prevention therapy to exert its most beneficial effects. Those of skill in the art will readily recognize and appreciate the value of developing prevention (i.e., preclinical AD) therapies. Such therapies are placing an increasing emphasis on the earliest possible detection of the brain changes associated with the predisposition to this disorder. Accordingly, the scientific community needs a new paradigm that reduces the impractically large subject samples, time, and cost currently required to establish the efficacy of putative preclinical AD prevention therapies, encourage industry and government agencies to sponsor the required trials, and prevent this growing problem without losing a generation along the way. The scientific community further needs a viable approach for evaluating putative treatment modalities on additional brain disorders other than AD, such as mild cognitive impairment (MCI), the decline in cognitive ability due to other age-related atrophy, or other disorders.

Drawbacks of Prior Imaging Processes used in Prevention Studies

Recently, researchers have begun using 18F-fluorodeoxyglucose (FDG) positron emission tomography (PET) and magnetic resonance imaging (MRI) to detect and track changes in brain function and structure which precede the onset of brain disorder symptoms in cognitively normal persons who are at risk for developing brain disorders such as Alzheimer's. Suggested risk factors for AD include older age, female gender, lower educational level, a history of head trauma, cardiovascular disease, higher cholesterol and homocysteine levels, lower serum folate levels, a reported family history of AD; trisomy 21 (Down's syndrome), at least 12 missense mutations of the amyloid precursor peptide (APP) gene on chromosome 21, at least 92 missense mutations of the presenilin 1 (PS1) gene on chromosome 14, at least 8 missense mutations of the presenilin 2 (PS2) gene on chromosome 1, candidate susceptibility loci on chromosomes 10 and 12, and the APOE $\epsilon$4 allele on chromosome 19.

Next to age, the APOE $\epsilon$4 allele is the best-established risk factor for late-onset AD. Thus, it is especially relevant to human brain imaging studies. The APOE gene has three major alleles, $\epsilon$2, $\epsilon$3, and $\epsilon$4. Compared to the $\epsilon$3 allele (the most common variant), the $\epsilon$4 allele is associated with a higher risk of AD and a younger age at dementia onset. The $\epsilon$2 allele, on the other hand, may be associated with a lower risk of AD and an older age at dementia onset.

In one of the original case-control studies, for instance, individuals with no copies of the $\epsilon$4 allele had a 20% risk of AD and a median age of 84 at dementia onset; those with one copy of the $\epsilon$4, which is found in about 24% of the population, had a 47% risk of AD and a median age of 76 at dementia onset. Those with two copies of the $\epsilon$4 allele (the $\epsilon$4/$\epsilon$4 genotype, found in 2-3% of the population) had a 91% risk of AD by 80 years and a mean age of 68 at dementia onset. In another study, 100% of $\epsilon$4 carriers with cognitive loss had neuritic plaques at autopsy. In a related study, 23% of their AD cases were attributed to absence of the $\epsilon$2 allele and another 65% of their cases were attributed to the presence of one or more copies of the $\epsilon$4 allele.

Case-control studies in numerous clinical, neuropathological, and community studies have confirmed the association between the $\epsilon$4 allele and AD. Farrer et al. conducted a worldwide meta-analysis of data from 5930 patients with probable or autopsy-confirmed AD and 8607 controls from various ethnic and racial backgrounds. In comparison with persons with the genotype $\epsilon$3/$\epsilon$3, the risk of AD was significantly increased in genotypes $\epsilon$2/$\epsilon$4 (odds ratio [OR]=2.6), $\epsilon$3/$\epsilon$4 (OR=3.2), and $\epsilon$4/$\epsilon$4 (OR=14.9), and the risk of AD was significantly decreased in genotypes $\epsilon$2/$\epsilon$3 (OR=0.6), and ~2/$\epsilon$2 (OR=0.6). Community-based, prospective studies promise to better characterize the absolute risk of AD in persons with each APOE genotype.

Prior imaging processes have focused on demonstrating that baseline reductions in structural or functional performance with a single imaging measurement predict subsequent clinical decline in patients with dementia and that baseline measurements in MCI predict higher rate of conversion to AD. But those findings have been unable to demonstrate that the selected brain imaging process is an adequate surrogate marker for demonstrating prevention of or delayed onset of a disease state. More specifically, the processes must be able to show that a surrogate marker correlates with clinical severity in patients. The processes must also be able to demonstrate that when a change in measurements is attributable to administration of a treatment regimen, the change in measurement also predicts an improved clinical outcome. Prior single baseline imaging techniques are insufficient in this regard.

According to Temple's commonly cited definition, a surrogate endpoint of a clinical trial is "a laboratory measurement or a physical sign used as a substitute for a clinically meaningful endpoint that measures directly how a patient feels, functions, or survives; changes induced by a therapy on a surrogate endpoint are expected to reflect changes in a clinically meaningful endpoint." According to Fleming and DeMets, a valid surrogate endpoint is not just a correlate of the clinical outcome; rather, it should reliably and meaningfully predict the clinical outcome and it should fully capture the effects of the intervention on this outcome. Citing several examples, they note several ways in which an otherwise promising surrogate endpoint might fail to provide an adequate substitute for a clinical endpoint.

Although few if any surrogate endpoints have been rigorously validated, the 1997 United States "FDA Modernization Act" authorizes the approval of drugs for the treatment of serious and life-threatening illnesses, including AD, based on its effect on an unvalidated surrogate. In order to promote the study and expedite the approval of drugs for the treatment of these disorders, "fast track" approval" may be granted if the drug has an effect on a surrogate marker that is "reasonably likely" to predict a clinical benefit; in such cases, the drug sponsor may be required to conduct appropriate post-marketing studies to verify the drug's clinical benefit and validate the surrogate endpoint.

Linking Functional and Structural Brain Images

Neuroimaging researchers frequently acquire a combination of functional and structural brain images. Examples of functional brain images include those obtained via positron emission tomography (PET) or functional magnetic resonance imaging (fMRI). An example of structural brain images include those obtained via volumetric MRI. Structural MRI data is often used in PET/fMRI studies for anatomical localization of functional alterations, definition of regions of interest for the co-registered PET/fMRI data extraction, and partial volume correction. Neuroimages have been most commonly analyzed using univariate methods. However, multivariate analyses have also been used to characterize inter-regional correlations in brain imaging studies. Multivariate algorithms have included principal component analysis (PCA), the PCA-based Scaled Subprofile Model (SSM), and the Partial Least Squares (PLS) method. These methods have typically been used to characterize regional networks of brain function (and more recently brain anatomy) and to test their relation to measures of behavior. Such multivariate methods, however, have not yet been used to identify patterns of regional covariance between functional and structural brain imaging datasets.

A major challenge to the multivariate analysis of regional covariance with multiple imaging modalities is the extremely high dimensionality of the data matrix created by including high-resolution neuroimaging datasets. The scientific community needs an advanced technology that can successfully compute, in a practical and useful fashion, dimensional datasets with a covariance analysis using multivariate methods.

As discussed above, another major drawback to previously existing methods and systems for evaluating prospective treatments for AD is that they fail to provide sufficient power to evaluate the treatments in a meaningful or useful way.

SUMMARY

In an embodiment, a method for evaluating a prospective treatment for Alzheimer's disease (AD) includes receiving at a computing device subject data concerning each of multiple human subjects. The subject data includes an age range, risk of Alzheimer's disease (AD), and the presence or absence of clinical symptoms of AD. The subjects are divided based on the subject data into a first group of subjects treated with a prospective AD treatment of interest and a second group of subjects not treated with the prospective AD treatment. Each subject is either a homozygote of apolipoprotein E (APOE) with two ϵ4 alleles associated with AD, a heterozygote of APOE with one ϵ3 and one ϵ4 allele associated with AD and mild cognitive impairment (MCI), or a non-carrier of alleles associated with AD who has no clinical symptoms of AD.

The method further includes storing the subject data concerning each of the subjects in memory of the computing device and receiving at the computing device a plurality of brain imaging measurements from an 18F-fluorodeoxyglucose (FDG) positron emission tomography (PET) scanner. For purposes of this disclosure, the term "brain imaging measurements" includes an image or scan containing measurements related to the brain. The brain imaging measurements indicate a cerebral metabolic rate for glucose (CMRgl) associated with each subject. The CMRgl is a potential surrogate marker found in the absence of treatment to be correlated with clinical severity of AD symptoms. The brain imaging measurements are arranged in a data matrix and are associated with a first voxel size.

The method also includes executing instructions stored in memory of the computing device. Execution of the instructions by a processor of the computing device resamples the brain imaging measurements with a second voxel size larger than the first voxel size to reduce a number of voxels of the measurements. Execution of the instructions further partitions the data matrix into a plurality of sub-matrices and reads the sub-matrices into memory of the computing device one at a time. The method includes, as the sub-matrices are read into memory one at a time, iteratively calculating a rate of change in CMRgl for the treated group of subjects during or following treatment with the AD therapy based on a predetermined interval. The method likewise includes iteratively calculating a rate of change in CMRgl for the untreated group of subjects over the same predetermined interval. The calculated rate of change for the untreated group is based on the brain imaging measurements for each subject in the untreated group over the same predetermined period of time.

Execution of the instructions further compares the rate of change calculated for the treated group to the rate of change calculated for the untreated group and determines whether a difference between the rate of change calculated for the treated group and the rate of change calculated for the untreated group is statistically significant. The determination as to whether the difference is statistically significant is made by referencing a cluster of voxels previously predetermined using a statistical threshold to characterize the brain regions that are preferentially associated with accelerated CMRgl decline in an independent chort of research participants meeting similar selection criteria who wer followed in the absence of any treatment. The cluster of preferentially affected brain voxels may be referred to as an empirically predefined "statistical region-of-interest" (sROI).

The method further includes determining an efficacy of the AD therapy and a validity CMRgl as a surrogate marker based on the difference between the rate of change for the treated group and the rate of change for the untreated group.

In another embodiment, a system for evaluating a prospective treatment for Alzheimer's disease (AD) includes an 18F-fluorodeoxyglucose (FDG) positron emission tomography (PET) scanner that takes a plurality of brain imaging measurements from each of a pool of human subjects. The brain imaging measurements indicate a cerebral metabolic rate for glucose (CMRgl) associated with each subject. The CMRgl is a potential surrogate marker found in the absence of treatment to be correlated with clinical severity of AD symptoms. The brain imaging measurements are arranged in a data matrix and are associated with a first voxel size. Each subject is either a homozygote of apolipoprotein E (APOE) with two ϵ4 alleles associated with AD, a heterozygote of APOE with one ϵ3 and one ϵ4 allele associated with AD and mild cognitive impairment (MCI), or a non-carrier of alleles associated with AD who has no clinical symptoms of AD. Alternatively, each subject may carry an autodomal dominant AD mutation or have biomarker evidence of AD pathology (e.g., a positive amyloid PET scan, etc) prior to the onset of symptoms.

The system further includes a computing device that has a processor and memory storing executable instructions. The computing device is communicatively coupled to the imaging device and receives the brain imaging measurements from the FDG-PET scanner. The computing device further receives subject data concerning each of the subjects. The subject data includes an age range, risk of Alzheimer's disease (AD), and the presence or absence of clinical symptoms of AD. The subjects are divided based on the subject data into a first group of subjects treated with a prospective AD treatment of interest and a second group of subjects not treated with the prospective AD treatment.

The computing device stores the subject data concerning each of the subjects in memory of the computing device executes instructions stored in the memory of the computing device. Execution of the instructions by the processor of the computing device resamples the brain imaging measurements with a second voxel size larger than the first voxel size to reduce a number of voxels of the measurements and partitions the data matrix into a plurality of sub-matrices. Execution of the instructions then reads the sub-matrices into memory of the computing device one at a time and iteratively calculates, based on a predetermined interval, a rate of change in CMRgl for the treated group during or following treatment with the AD therapy and a rate of change in CMRgl for the untreated group. Execution of the instructions causes the computing device to determine that a difference between the rates of change in CMRgl calculated for the treated and untreated groups is statistically significant and, in doing so, indicates that the AD therapy is efficacious and CMRgl is a valid surrogate marker.

DETAILED DESCRIPTION

Figure 1:
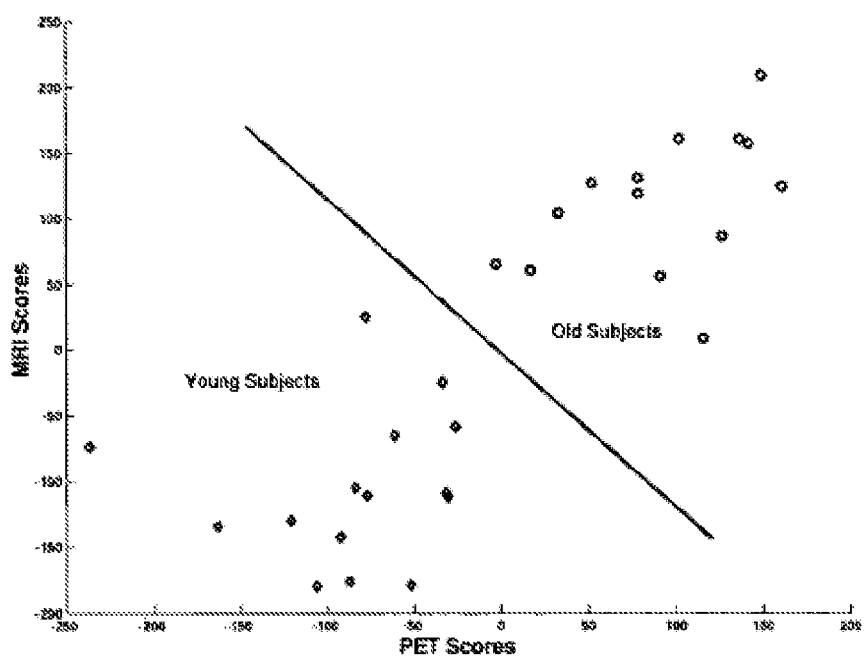
FIG. 1 depicts a graph indicating the absence of overlap between younger subjects (as seen by the diamonds) and older subjects (as seen by the circles) using the combination of PET and MRI scores, where the combination of scores maximized group separation.

Exemplary embodiments of advanced systems and methods for evaluating the efficacy of prospective preventative treatments for Alzheimer's disease ("AD"). Ultimately, the efficacious treatments evaluated in accordance with the systems and methods aim to contribute to improved clinical outcomes in patients at risk for brain-related disorders. Embodiments of the systems and methods described herein apply advanced computational algorithms for the voxel-based analysis of brain images to track longitudinal changes and evaluate investigational prevention therapies with improved power, making the use of these and other biomarker endpoints practical for use in AD prevention trials. Without the systems and methods disclosed herein, brain imaging measurements cannot be analyzed with sufficient power to evaluate prospective AD prevention treatments in a practical way.

The use of brain imaging measurements or fluid biomarkers to track changes that provide meaningful information about preclinical AD allows for a practical method of studying AD that avoids the sample size, study length, and cost problems associated with methods in the prior art. In addition to the various features described herein, including the methods for making the various computational steps functionally practical, the study of persons at risk for AD by virtue of other biomarker evidence of preclinical AD or the combination of their age and generic risk factors is in and of itself a novel and promising method for evaluating prospective treatments for AD.

The following description is exemplary only and in no way limits the scope of the inventive concepts detailed herein. Although certain exemplary embodiments are described, persons of ordinary skill in the art will readily recognize and appreciate that the embodiments were selected to most clearly illustrate the inventive concepts without unduly diluting the same and that other variations and embodiments are implicitly possible in view of the present disclosure.

FDG-PET measurements of posterior cingulate, parietal, temporal, and prefrontal CMRgl and volumetric MRI measurements of hippocampal, entorhinal cortex, and whole brain volume are promising surrogate markers for the assessment of putative drugs in the treatment of AD. These surrogate endpoints are not rigorously validated, partly because validation may actually require demonstration of these endpoints to account for the predicted clinical effect using several established disease-modifying treatments. Still, these brain imaging measurements are "reasonably likely" to predict a drug's clinical benefit in the treatment of AD. Investigators associated with the present invention are also conducting prevention trials in cognitively unimpaired persons at particularly high imminent risk for the clinical onset of AD to show a relationship between the treatments' two-year effects on many of the promising but unvalidated biomarkers and their clinical outcome. If there is a relationship between an effective treatment's biomarker and clinical effects, the biomarker would have the potential to qualify for use as a reasonably likely surrogate endpoint for use in future license-enabling prevention trials. They have much greater statistical power than traditional outcome measures, which reduces the potential cost of proof-of-concept studies. Along the same thread, they are "reasonably likely" to determine a drug's disease-modifying effects, helping to distinguish a drug's disease-modifying from symptomatic effects.

As discussed below, these brain-imaging measurements may permit the efficient discovery of prevention therapies in cognitively unimpaired persons at risk for AD. They may also assist in the pre-clinical screening of candidate treatments in transgenic mice and other putative animal models of AD. For all of these reasons, FDG-PET and volumetric MRI are important and have emerging roles in the evaluation of putative disease-modifying candidate drugs in the treatment and prevention of AD.

In various embodiments, the systems and methods described herein may include one or more of: the use of an imaging device (e.g., FDG-PET, amyloid and tau PET, structural MRI, functional connectivity MRI, etc.) with an axial field-of-view that covers the entire brain; data acquisition in the three-dimensional mode, thus permitting the use of lower radiation doses; the use of a non-invasive, image-derived input function, thus permitting the computation of quantitative measurements (in case CMRgl reductions are so extensive that they affect measurements in the whole brain or relatively spared regions, like the pons, that would otherwise be used to normalize images for the variation in absolute measurements); data acquisition in the "resting state" (e.g., eyes closed and directed forward) rather than during the performance of a behavioral task (because the resting state has been used most extensively to track the progression of CMRgl changes in patients with AD and cognitively unimpaired persons at risk for the disorder and since any effects of a drug on task performance could confound interpretations about the drug's putative disease-modifying effects); the use of an automated brain mapping algorithm to characterize and compare regional CMRgl declines in the active treatment and placebo treatment arms (e.g., those involving statistical parametric mapping); quality assurance procedures to maximize the quality and standardization of image-acquisition and image-analysis procedures at different sites; and a single site for the technical coordination and the centralized storage and analysis of data in multi-center studies.

Embodiments of the systems and methods describe herein may further include one or more of: processes that control or account for potentially confounding effects, such as medication effects (e.g., stratifying samples for use of an approved medication, discouraging the introduction of new medications during the trial, and minimizing or accounting for the use of medications prior to the PET session) and changes in depression ratings; the use of baseline, early, and end-of-treatment scans (performance of the early scan after a drug's steady state and relevant pharmacodynamic effects would help characterize and contrast a medication's state-dependent effects on local neuronal activity or glucose metabolism and its disease-modifying effects); and the use of additional scans as indicated (e.g., to evaluate the time course of an effect, increase statistical power, or incorporate a randomized start or withdrawal design).

Even if a user does not need data to support an accelerated drug approval pathway, embodiments of the systems and methods described herein are nevertheless useful for relating a drug's short-term effects on surrogate endpoint (e.g., 24-month effects in cognitively unimpaired persons at risk for AD to 60-month clinical effects, as in the design of the Alzheimer's Prevention Initiative (API) trials. Such information helps to validate the use of surrogate markers and support the use of shorter study intervals for the future study of the candidate drugs (and other candidate drugs).

Methods for evaluating a prospective treatment for AD are disclosed. Embodiments of the following methods include an advanced computational imaging process that permits the evaluation of longitudinal changes in brain imaging measurements (for instance, in a statistical region of interest that includes the cluster of voxels associated with maximal changes) and provides a way to evaluate prospective AD treatments with greater power than any prior method. In some embodiments, the computational imaging process permits the evaluation with only a single measurement, a feature that avoids statistical problems presented by Type 1 errors in multiple regional comparisons attempted in the prior art.

In one embodiment, an advanced method for evaluating a prospective treatment for Alzheimer's disease and other progressive brain disorders may include receiving subject data concerning each of a plurality of human subjects. The subject data may be received at a computing device having a processor, memory storing executable instructions, and, in some cases, a network interface communicatively coupled to a communications network. In some embodiments, the computing device may be associated with a user, such as a clinician or laboratory staff, and the subject data may be received through a graphical user interface displayed on a display of the computing device. The computing device may be a desktop computer, a laptop, or any number of mobile devices with sufficient processing power to complete the computational analyses described herein. Such mobile devices may include tablets, smartphones, or any other mobile device now known or later developed. The subject data may also be received from an intermediate computing device or other computing device not necessarily associated with a user, such as a server.

The plurality of human subjects may be divided into two more groups based on the subject data. For instance, the human subjects may be divided into: (1) a first group of subjects treated or designated to be treated with a prospective AD treatment of interest; and (2) a second group of subjects not treated and designated to remain untreated for the same prospective AD treatment of interest.

Concerning either or both groups, the subject data may include demographic data, such as a particular subject's age and whether the subject falls into a predetermined age range, risk-related data, such as the subject's risk of developing AD at some point in the future, and clinical data, such as data concerning the presence or absence of clinical symptoms of AD. The subject data may further include genetic data, such as whether the subject is a carrier of certain alleles that, when present in a human subject, are known to influence the risk of developing AD at some point in the future.

In one embodiment, the genetic data may include whether the subject is a carrier of a particular allele of the apolipoprotein E (APOE) gene and, if so, whether the subject is a heterozygote (i.e., carries two different APOE alleles, such as one $\epsilon3$ allele and one $\epsilon4$ allele) or a homozyote (i.e., carries two of the same APOE alleles, such as two $\epsilon4$ alleles). Relatedly, the genetic data may include whether the subject is a non-carrier of the APOE allele. In some embodiments, all or a portion of the subjects may be associated with mild cognitive impairment (MCI). Moreover, all or a portion of the subjects may have no clinical symptoms of AD. In various embodiments, the treated and untreated groups may include a combination of the homozygotes, heterzygotes, and non-carriers described above. The precise combination of such subjects will depend on a number of numerous study design considerations.

The method may further include storing the subject data in the memory of the computing device. The subject data may be stored in a database or other fashion suitable for ensuring that the processor of the computing device may access the data at a later date. The method may also include receiving for each of the subjects a plurality of brain imaging measurements from an imaging device. The brain imaging measurements may be received at the computing device. The network interface of the computing device may be communicatively coupled to the imaging device over a network to facilitate wireless transmission of the brain imaging measurements from the imaging device to the computing device. The imaging device and the network interface of the computing device ma by communicatively coupled either directly or through one or more intermediate computing devices. In some embodiments, the imaging device and the computing device may be directly coupled so as not to rely on a communications network and to ensure that any prospective disruption in such a network will not disrupt receipt of the brain imaging measurements at the computing device.

The brain imaging measurements may measure a surrogate marker that, when detected by the imaging device in the absence of treatment is correlated with clinical severity of AD symptoms. For instance, as discussed below in further detail, in one embodiment the brain imaging measurements may be measurements of cerebral metabolic rate for glucose (CMRg1) detected by a FDG-PET scanner. In such a case, the detected presence of elevated CMRg1 detected by the FDG-PET scanner may be correlated with an increased likelihood of the subject developing AD symptoms in the future and, if so, the clinical severity of those symptoms.

The brain imaging measurements may, in some embodiments, be transformed into a voxel-based data matrix. The imaging data may be associated with a first voxel size. Due to the significant size of the imaging data received at the computing device, the method may include resampling the imaging data. Resampling the imaging data may include resampling with a second voxel size larger than first voxel size. By increasing the size of each voxel, the overall number of voxels may be reduced.

The method may further include partitioning the data matrix into a plurality of sub-matrices and reading the sub-matrices into memory of the computing device one at a time at a rate determined by when the processor of the computing device requires each sub-matrix to iteratively process the imaging data stored in the data matrix. Iteratively processing the imaging data may include calculating a rate of change for the subjects in the treated group either during or following treatment with the prospective AD treatment at issue over a predetermined period of time. Iteratively processing the imaging data may include calculating a rate of change for the subjects in the untreated group over substantially the same predetermined period of time.

Iteratively processing the imaging data may further include comparing the rate of change calculated for the treated group to the rate of change calculated for the untreated group and determining whether any difference between the rate of change calculated for the treated group and the rate of change calculated for the untreated group is statistically significant. Whether or not the calculated difference is statistically significant may be determined by comparison to a predetermined statistical threshold.

The method may include determining an efficacy of the prospective AD therapy at issue and/or validating the surrogate marker based on the calculated difference between the rate of change for the treated group and the rate of change for the untreated group.

As noted above, in on embodiment subjects may be ε4 homozygotes, ε4 heterozygotes (all with the ε3/ε4 genotype), and ε4 non-carriers who are initially late middle-aged (i.e., younger than the suggested median onset of AD) and cognitively normal. The subjects may be individually matched based on the subject data, which in addition to demographic data such as gender and age, may contain other data related to the subjects' education level. In such embodiments, because individuals with the ε4/ε4 genotype have an especially high risk of AD, studying that particular subject group optimizes the power to characterize the brain and behavioral changes that precede the onset of cognitive impairment. Accordingly, such embodiments allow for correlations between these changes and the subsequent onset of MCI and AD. Additionally, because individuals with the ε3/ε4 genotype have an increased risk of AD and comprise about 20-23% of the population, the study of that particular subject group extends the findings to a larger segment of the population and increases the number of individuals who would be eligible to participate in future clinical trials of putative preclinical AD prevention therapies.

In one embodiment, the brain imaging measurements may be obtained from ε4 noncarriers who are individually matched for gender, age, and educational level. Doing so may optimize the power to characterize the brain and behavioral changes associated with normal aging and allow the changes to be distinguished from age-related changes preferentially related to the presence of the ε4 allele and the subsequent onset of AD.

Importantly, the foregoing approach is not limited to utilizing APOE genotype as the relevant risk factor for AD. Persons of ordinary skill in the art will readily recognize that other risk factors, including those now known or discovered in the future, may be utilized in connection with the systems and methods described herein to study cognitively normal persons who are at differential risk for AD independent of (or in conjunction with) their APOE genotype.

PET Imaging Device

In one embodiment, the imaging device may be a position emission tomography (PET) scanner, such as an [$^{18}$F] fluorodeoxyglucose (FDG) PET scanner. The brain imaging measurements provided by the FDG-PET scanner and received at the computing device may be image-based measurements of the cerebral metabolic rate for glucose (CMRgl) for each subject. The brain imaging measurements provided by the FDG-PET may also include other indications of characteristic abnormalities in patients with AD, including abnormally low posterior cingulate, parietal, and temporal CMRgl, abnormally low prefrontal and whole brain CMRgl in more severely affected patients, and a progressive decline in these and other measurements over time. These abnormalities, which are correlated with dementia severity and predict subsequent clinical decline and the histopathological diagnosis of AD, may be related to a reduction in the activity or density of terminal neuronal fields or perisynaptic glial cells that innervate these regions, a metabolic dysfunction, or a combination of these factors. These abnormalities detected by FDG-PET do not appear to be solely attributable to the combined effects of atrophy and partial-volume averaging.

Importantly, brain abnormalities can be detected prior to the onset of dementia. Prior studies have shown that, in comparison with the ε4 noncarriers, the ε4 homozygotes and heterozygotes each have abnormally low CMRgl in the same brain regions as patients with probable AD. Despite no significant differences in clinical ratings or neuropsychological test scores and no significant interactions between these measurements and time, the ε4 heterozygotes have significantly higher 2-year rates of CMRgl decline. Based on that data, an estimated power of PET may be used to test the efficacy of candidate prevention therapies that may attenuate this decline in 2 years.

In complementary PET studies of cognitively unimpaired ε4 carriers and noncarriers who were about 10 years older, the ε4 carriers had memory concerns, and had slightly lower MMSE scores; furthermore, lower CMRgl measurements in the posterior cingulate and parietal cortex were correlated with a subsequent decline in memory.

While it remains possible that the CMRgl abnormalities reflect aspects of the ε4 allele unrelated to AD, PET studies suggest that these abnormalities are in fact related to the development of AD. While there may be a few differences, patients with probable AD appear to have a similar pattern of reductions in regional CMRgl whether or not they have the ε4 allele. And, as previously noted, the CMRgl abnormalities in patients with probable AD serve as a useful predictor of the future progression of dementia and the histopathological diagnosis of AD, are progressive, and are correlated with dementia severity.

In another embodiment, the imaging device may be a PET device that utilizing radiotracer techniques, such as methylpiperidinyl propionate (PMP) PET. PMP PET provides estimates of acetylcholinesterase activity and can detect deficits in patients with probable AD. PMP PET may be used to evaluate the extent of central inhibition by established or investigational acetylcholinesterase inhibitors and help optimize dosage schedules.

In another embodiment, the imaging device may be a (R)-PK11195 PET device that provides estimates of peripheral benzodiazepine receptor binding, a putative marker of neuroinflammation. (R)-PK11195 PET can detect abnormally increased measurements and herald the subsequent onset of atrophy in patients with probable AD and, as a result, may be used to track the course of neuroinflammation in AD and characterize the central anti-inflammatory effects of medications.

Embodiments of the advanced systems and methods disclosed herein may include collecting subject data and brain imaging measurements from cognitively normal persons at differential genetic risk for AD. In an initial step, subjects who deny any memory concerns and are medically well may be recruited using newspaper ads or other suitable methods. The subjects may be required to agree that they will not receive any information about their APOE genotype (because this information cannot be used to predict with certainty whether or when a person will develop AD) and may provide their informed consent. In a further step, blood samples may be drawn and APOE genotypes may be characterized. In another step, for each APOE ε4 carrier who agrees to participate in the imaging trial, one ε4 noncarrier may be matched for his or her gender, age (within 3 years or some other predetermined threshold range), and educational level (within 2 years or some other predetermined threshold range).

The method may further include using FDG-PET to take quantitative measurements of CMRgl of subjects. In some embodiments, taking the measurements may include having the subjects rest quietly with their eyes closed. The method may further include measuring volumetric changes in the brain using volumetric T1-weighted MRI. In some embodiments, the method may further include one or more of a clinical examination, a structured psychiatric interview, a depression rating scale, a Folstein Mini-Mental State Examination (MMSE), and any number of suitable neuropsychological tests and psycholinguistic tasks.

In one embodiment, the quantitative measurements of CMRgl taken using FDG-PET and/or the volumetric measurements taken using volumetric T1-weighted MRI (or any other suitable measurement obtained in accordance with the presently disclosed systems and methods) may be acquired repeatedly at predetermined intervals. In one embodiment, for instance, taking the foregoing measurements may include taking the measurements every 2 years. For instance, taking the measurements every 2 years may be suitable in an embodiment involving 160 cognitively normal and individually matched ∈4 homozygotes, heterozygotes, and noncarriers 47-68 years of age with a reported first-degree family history of probable AD. In other embodiments, the measurements may be characterized and compared in cognitively normal ∈4 carriers and noncarriers 20-80 years of age (or another predetermined elderly age) irrespective of their reported family history or probable AD.

In one embodiment, the systems and methods described herein may determine that cognitively normal, late middle-aged APOE ∈4 homozygotes at a particularly high risk of AD have abnormally low PET measurements in the same brain regions as patients with probable AD. APOE genotypes may be characterized in cognitively normal persons 50-65 years of age with a reported first-degree family history of probable AD. For each of the ∈4 homozygotes who agree to participate in the imaging process, 2 ∈4 noncarriers may be matched for their gender, age (within 3 years or some other predetermined threshold range), and educational level (within 2 years or some other predetermined threshold range). For instance, in one exemplary scenario, the ∈4 homozygotes may have a mean age of 55 (within a range of 50-62), a mean MMSE score of 29.4 (with a range of 28-30), and no significant differences from the controls in their clinical ratings or neuropsychological test scores.

Figures 3, 4:
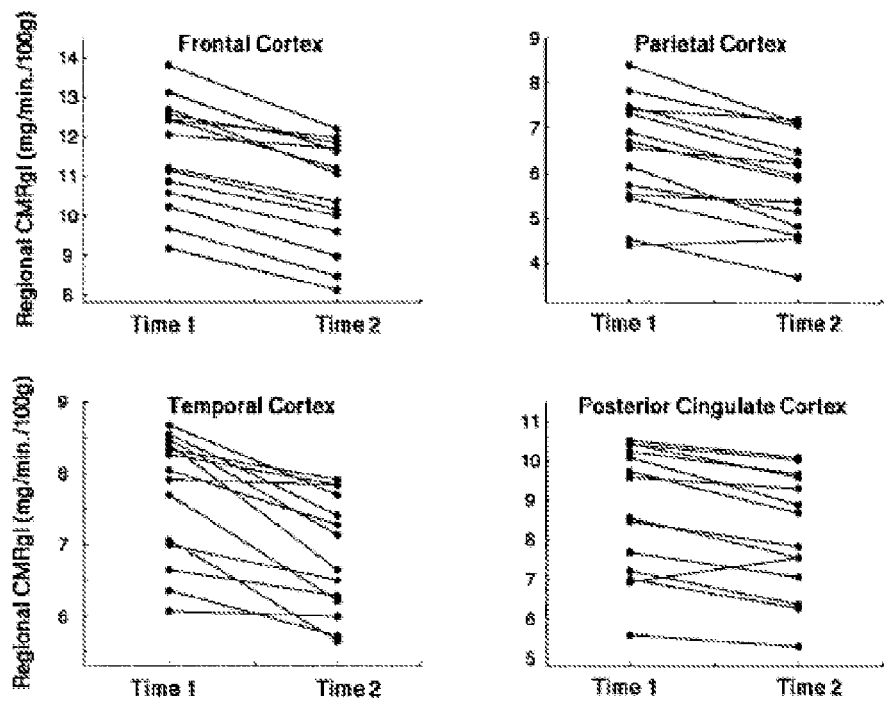
FIG. 3 illustrates that patients with probable Alzheimer's Disease have abnormally low CMRgl bilaterally in posterior cingulate, parietal, temporal, and prefrontal cortex.
FIG. 4 illustrates benefits associated with using a volumetric MRI machine to study declines in brain volume.

In one embodiment, executable instructions stored in memory of a computing device may, when executed, apply an automated brain mapping algorithm that generates a three-dimensional stereotactic surface projection statistical map. The map may facilitate characterizing regions of the brain with abnormally low CMRgl in patients with probable AD by comparing the data from patients with probable AD to normal controls (mean age 64). In some instances, the maps may reveal that patients with probable AD have, as illustrated in FIG. 3, abnormally low CMRgl bilaterally in posterior cingulate, parietal, temporal, and prefrontal cortex, the largest of which was in the posterior cingulate cortex.

Execution of the instructions may further apply the automated brain mapping algorithm to create a three-dimensional surface projection statistical map comparing data from homozygotes and non-carriers. The map may facilitate characterization of brain regions having reduced CMRgl in the cognitively normal ∈4 homozygotes. In some embodiments, as shown in FIG. 1, the map may further be superimposed onto the map of CMRgl abnormalities in the patients with probable AD to help further characterize the brain regions having reduced CMRgl.

Embodiments of the foregoing method may track longitudinal declines in FDG PET measurements of CMRgl decline in a statistical region of interest. The region of interest may include a cluster of voxels associated with maximal decline in AD, thus providing a mechanism to evaluating AD-modifying treatments with greater power than and other method known in the prior art. The method may do so in a single measurement, thus avoiding the statistical problem of Type 1 error related to multiple regional comparisons in the prior art.

Notably, the method may be applied to the analysis of any functional or structural brain imaging data prior to the onset of symptoms, such as a measure of medial temporal atrophy. The method may include conducting voxel-based analyses of FDG-PET images using spatial parametric mapping. The method may include a step of training data sets and confirming the power of the method with independent test data sets. For example, the determined statistical region of interest may be customized to particular subject samples and study durations using voxel-based image-analysis techniques. For instance, a statistical region of interest may be empirically predefined in AD and MCI patient training sets using spatial parametric mapping.

As noted above, the method may be used to develop a statistical region of interest in cognitively unimpaired APOE ∈4 homozygotes and to estimate the number of subjects and treatment effect sizes in a subsequent study. The method disclosed herein constitutes the only method with demonstrated power to track the FDG-PET changes that occur prior to the onset of AD-related cognitive impairment or revaluate AD prevention therapies.

In one embodiment of the method, baseline and twelve-month follow-up FDG PET scans may be acquired according to a standardized protocol on a plurality of different PET Scanners. The scanners may be any of a variety of models manufactured by well-known manufacturers such as GE, Philips, and Siemens. The method may include the imaging device (in this case an FDG PET scanner) collecting brain imaging measurements by performing a 30-min dynamic emission scan consisting of six 5-min frames. The scan may be acquired starting 30 min after the intravenous injection of 5 mCi of $^{18}$F-FDG. The subjects may be required to fast prior to the scan, lay quietly in a dimly lit room with their eyes open and with minimal sensory stimulation. Data may be corrected for radiation-attenuation and scatter using transmission scans or X-ray CT, and reconstructed using reconstruction algorithms specified for each type of scanner. Each dynamically acquired image may be reviewed and pre-processed to identify artifacts and minimize scanner-dependent differences in FDG uptake.

During the pre-processing stage, automated algorithms may be used to register and average each subject's six 5-min emission frames, transform each subject's registered image into a 160×160×1.5 mm voxel matrix with sections parallel to a horizontal section through the anterior and posterior commissures (without any adjustment for size or shape), normalize the images for individual variations in absolute image intensity, and apply a filter function previously customized for each scanner using a Hoffmann brain phantom scanned during the a qualification process to ensure an isotropic spatial resolution of 8 mm full-width-at-half-maximum (FWHM).

As noted above, the imaging data may be receiving by a computing device where it may be analyzed in accordance with the methods and systems described herein. The baseline and twelve-month follow-up image pair for each subject may first be aligned to each other. The image pairs may then be linearly and nonlinearly transformed to the Montreal Neurological Imaging (MNI) Template and smoothed using a Gaussian kernel. Regional PET count data may be normalized for the variation in measurements from whole brain, an empirically characterized "spared ROI," or other candidate reference ROIs using proportional scaling. Then, the region PET count data may be used to compute statistical maps of twelve-month CMRgl declines.

In order to characterize twelve-month CMRgl declines, data from both the training and test data sets may be used in each patient group. The training dataset may subsequently be used to optimize the settings used to empirically define the procedures associated with maximal twelvemonth sROI CMRgl declines in each patient group. As discussed above, the test dataset may ultimately be used to estimate the number of patients needed to detect treatment effects in each patient group in a twelve-month RCT using the empirically pre-defined settings and sROI.

To characterize twelve-month CMRgl decline in each patient group, the baseline and twelve-month follow-up images from both the training and test datasets may further be smoothed with aGaussian kernel with 12 mm maximum (FWHM). In one embodiment, whole-brain imaging measurements may be computed using the spm_global subroutine and may be used to normalize the baseline and twelve-month follow-up scans for the individual variation in whole-brain measurements. The general linear model (GLM) based simple t-test may be used to examine the twelve-month CMRgl difference images in each subject group. Further, the independent two-sample t-test may be used to compare the CMRgl decline difference in each patient group to that in the NCs.

In the training data set, sROI declines may be characterized using a combination of a) different FWHM values of the smoothing Gaussian kernel; b) brain imaging measurements from different candidate reference regions to normalize PET images for the individual variation in absolution PET counts; and c) different t-score thresholds to define the cluster of voxels in the candidate sROI. The FWHM values of the Gaussian smoothing kernel, candidate reference regions, and candidate sROI t-score thresholds are described below. An SPM5 voxel-based statistical procedure may be repeatedly applied in batch mode to the baseline and twelve-month follow-up images from the probable AD patient and MCI patient training datasets, respectively, to identify the optimal combination of the candidate settings noted above and detailed below to empirically define an sROI consisting of the set of voxels associated with the most significant twelve-month sROI CMRgl declines in each patient group.

The optimal FWHM of the smoothing kernel, reference region, and sROI may then be applied to the respective patient group's independent test dataset to estimate the number of patients needed to detect a 25% effect of an AD-slowing treatment a 25% slowing of the CMRgl decline in the sROI) with 80% power, two-tailed $\alpha=0.05$, and no need to correct for multiple regional comparisons in a twelve-month RCT.

The foregoing method provides greater statistical power than that using ROIs defined using anatomical landmarks, which may not correspond closely to the set of voxels with maximal CMRgl decline. In contrast to the use of the individual atlas coordinates associated with maximal CMRgl decline, the foregoing method also provides a single comparison.

In the following paragraphs, exemplary procedures used to find the optimal combination of the smoothing Gaussian kernel FWHM, reference region, and sROI significance threshold to characterize twelve-month CMRgl declines using the probable AD and MCI training data sets are described. The training data set may be used to determine the best reference region to normalize baseline and twelve-month follow-up scans for the variation in PDC PET measurements in each patient group. The candidate regions may include whole-brain, pontine, cerebellar, somatosensory, motor, or thalamic regions suggested to be relatively spared in AD patients, and relatively spared sROIs. Whole-brain measurements may be automatically defined using the spm_global sub-routine. Somatosensory, motor, and thalamic ROI measurements may be automatically characterized using the automatic anatomical labeling (AAL) routine in SPM5. Relatively spared sROIs may be empirically defined from t-score maps as the set of voxels associated with twelve-month regional-to-whole-brain CMRgl increases using the General Linear Model in SPM5, proportional scaling for the variation in whole-brain measurements, and several different thresholds 0.01, 0.005, 0.001, 0.0005, 0.0001, 0.00005, and 0.00001, uncorrected for multiple comparisons).

In addition to the scanner specific smoothness applied to the images, the subject group's training set may also be also used to evaluate the effects of applying Gaussian kernels of different FWHM sizes, i.e., 0 mm (no smoothing), 5 mm, 8 mm and 12 mm. Different voxel-level statistical thresholds of $p=0.01$, 0.005, 0.001, 0.0005, 0.0001, 0.00005, and 0.00001 (uncorrected for multiple comparisons) may be applied to define the spatially distributed cluster of voxels associated with twelve-month CMRgl decline in each patient group, and may also be evaluated using the training dataset.

Statistical parametric mapping (e.g., SPM5) may be repeatedly performed in batch mode using every combination of normalization factors, smoothness, and sROI significance thresholds noted above to find the best normalization factor, smoothness and sROI to apply to each patient group's test set, characterize twelve-month sROI CMRgl declines and estimate the number of patients needed to detect AD-slowing treatment effects on these declines with no need to correct for multiple comparisons.

The reference regional normalization factor, smoothness, and the sROI determined from the training dataset may subsequently be used to characterize twelve-month CMRgl declines in the respective patient group's independent test dataset. This sROI may be applied to the independent testing datasets to estimate the number of mildly affected probable AD and amnestic MCI patients, respectively, needed per group to detect an AD-slowing treatment effect (e.g., reflecting 25% mean sROI/spared ROI CMRgl decline reduction observed in the treatment group as compared to no decline reduction in the placebo group) with 80% power and two-tailed $\alpha=0.05$ in a twelve-month, multi-center, double-blind, parallel group, placebo-controlled randomized clinical trial.

Sample size estimates may be computed using the standard procedure for two-independent samples as recommended by the ADNI biostatistical core. They also used the same procedure to characterize and compare sample size estimates using different imaging modalities; image-analysis procedures, and clinical ratings. The sample size estimates were based on twelvemonth sROI/spared CMRgl decline ratios in the probable AD group and the MCI group, respectively. The sROI CMRgl decline with clinical (ADAS-cog, CDR-SB and MMSE) declines may be corrected and compared to sROI power results based on clinical (ADAS-cog, CDR-SB, and MMSE) endpoints. The sROI defined for AD may also used in the NC group testing dataset; permitting the comparison of mean sROI declines in each group using analysis of covariance (ANCOVA).

Since an AD-slowing treatment may not be able to attenuate the brain changes associated with normal aging, a power analyses providing accounting for the mean sROI/spared ROI CMRg1 declines associated with "normal aging" may also be performed using the mean decline in the NC group (i.e., reflecting 25% of the difference between the mean twelve-month sROI, spared ROI CMRg1 decline anticipated in the placebo group and the mean decline in the NC group.)

MRI Imaging Device

As shown in FIG. 4, in another embodiment, the imaging device may be a volumetric MRI machine. For instance, the imaging device may be a 1.5 T Signa system produced by General Electric of Milwaukee, Wis. The brain imaging measurements provided by the volumetric MRI machine and received at the computing device may include image-based measurements of brain atrophy. Such measurements may reveal abnormally high brain atrophy in patients with probable AD. The brain imaging measurements may include progressive reductions in the volume of the hippocampus, entorhinal cortex, and whole brain, as well as progressive enlargement of the ventricles and sulci. Abnormal brain atrophy may be revealed through progressive reductions in the volume of the hippocampus, entorhinal cortex, and whole brain, as well as though progressive enlargement of the ventricles and sulci. The brain imaging measurements may be structural in nature and may include T1-weighted volumetric MRI measurements. In such cases, the structural brain imaging measurements may be useful for early detection and tracking of AD. Accordingly, the systems and methods provide greater opportunities for the assessment of candidate treatments that might modify disease progression.

MRI studies have found significantly smaller hippocampal volumes in patients with probable AD and cognitively unimpaired persons at risk for AD, correlations between reduced hippocampal volume and the severity of cognitive impairment, and progressive declines in hippocampal volume during the course of AD. A prior method of characterizing entorhinal cortex volume used in the early detection and tracking of MCI and AD includes the use of a semi-automated method for the measurement of whole brain atrophy. Whole brain atrophy is measured in individual human subjects following the coregistration and digital subtraction (DS) of MRIs. This prior method is known as the "digital subtraction method" or the "brain boundary shift integral" method. At least one limitation associated with the digital subtract method is that it is partly manual in nature. Specifically, it required manual editing to identify brain tissue voxels. The digital subtraction method also requires normalization for between-scan differences in voxel intensity.

Embodiments of the systems and methods disclosed herein improve upon the prior digital subtraction method by using a fully automated algorithm for measuring brain atrophy from sequential MRIs. In some embodiments, an iterative principal component analysis (IPCA) may be executed when iteratively processing the imaging data to comparing the rate of changes and determining whether the calculated difference is statistically significant may be determined by comparison to a predetermined statistical threshold.

Such embodiments may be used to study patients with AD, cognitively normal APOE ϵ4 homozygotes, heterozygotes, and noncarriers, or even transgenic mice. For instance, in one embodiment, the imaging device may be capture brain imaging measurements using a T1-weighted pulse sequence (radiofrequency-spoiled gradient recall acquisition in the steady state, repetition time=33 msec, echo time=5 msec, alpha=30°, number of excitations=1, field-of-view=24 cm, imaging matrix=256×92, slice thickness=1.5 mm, scan time=13:36 minute) was used to acquire 124 contiguous horizontal MRI slices with in-plane voxel dimensions of 0.94×1.25 mm. The T1-weighted MRIs may be examined visually to ensure their freedom from artifacts, lacunar infarcts, and other clinically significant brain abnormalities. The T1-weighted MRIs may then be analyzed to compute whole brain atrophy rates using the aforementioned iterative principal component analysis. More specifically, utilizing each subject's sequential MRIs, the iterative principal component analysis may be performed to characterize and compare whole brain atrophy rates in the three genetic groups (14-17) and to characterize correlations between APOE ϵ4 gene dose and the rate of whole brain atrophy. The iterative principal component analysis effectively computes whole brain atrophy as the difference between the number of voxels that reflect tissue loss and the number of voxels that reflect tissue gain. Unlike the digital subtraction method found in the prior art, embodiments of the iterative principal component analysis do not require manual editing and do not require normalization for between-scan differences in voxel intensity. Rather, the iterative principal component analysis is fully automated.

Figure 2:
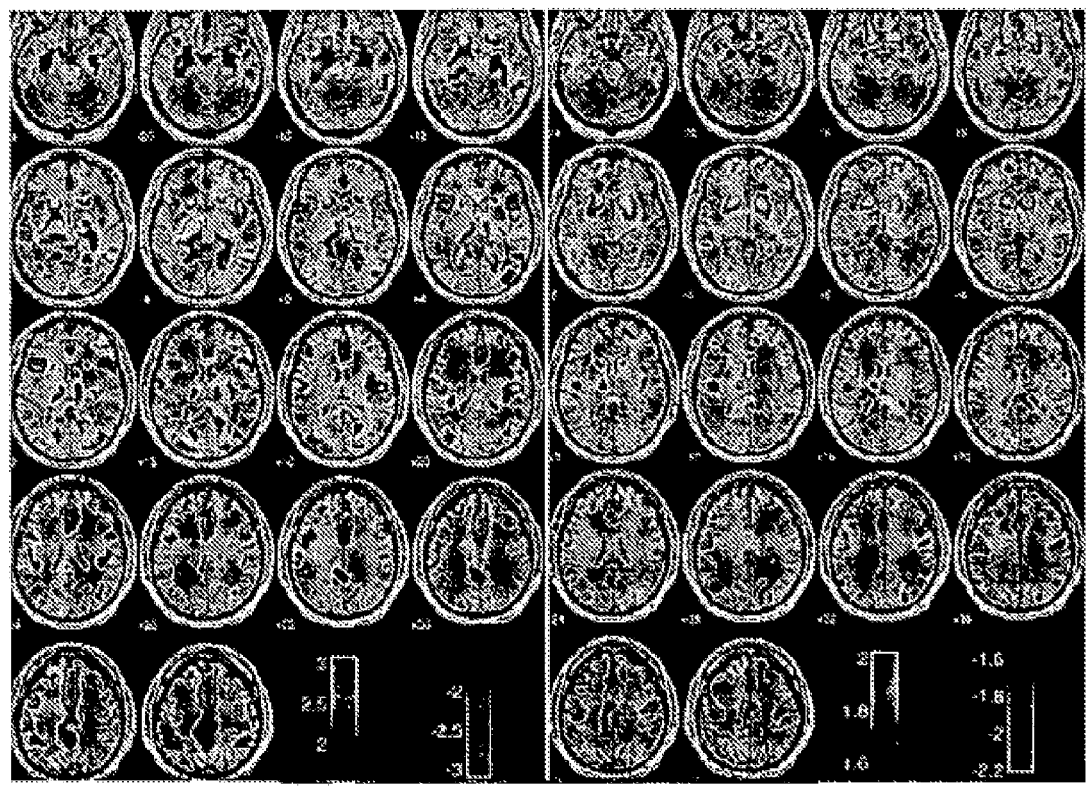
FIG. 2 shows first singular PET (left) and MRI images (right), wherein reduced cerebral metabolic rate for glucose (CMRgl) and gray matter concentration were each observed in the vicinity of medial frontal, anterior cingulate, bilateral superior frontal and precuneus cortex; lower CMRgl was observed in the absence of lower gray matter concentration in the vicinity of the posterior cingulate and bilateral inferior frontal cortex; and measurements of CMRgl and gray matter concentration were each relatively preserved in the vicinity of occipital cortex and the caudate nucleus.

In one embodiment featuring the iterative principal component analysis each a follow-up MRI of each subject may be initially coregistered to a baseline MRI of the subject using a realignment algorithm of a statistical parametric mapping program (for instance, the realignment algorithm available in the SPM99 software package distributed by the FIL Methods Group in the United Kingdom). The realignment algorithm may be modified to permit the correction for potential between-scan drifts in voxel dimensions. Brain volume may be defined automatically with the SPM99 brain extraction tool, which may be refined to automatically exclude any remaining nonbrain tissue. Paired voxel intensities over whole brain volumes may then be plotted to iteratively determine a ray (the major axis of the principal component analysis) around which the majority of the voxel-intensity pairs form an elongated narrow region (as shown in FIG. 2).

The iterative principal component analysis may further be used to identify the atrophy/gain as the voxel-intensity pairs whose distances to the ray are greater than a threshold distance. The threshold distance may be predetermined to optimize the trade-off between sensitivity and specificity. Finally, the between-scan change in brain volume may be translated into percent volume change per year relative to baseline intracranial volume.

In an embodiment, some steps of the statistical analyses may be performed using an off-the-shelf computer package such as SPSS 11.0. Annualized whole brain atrophy rates (i.e., the net loss in brain volume as a percent of baseline brain volume per year) may be initially compared in the three subject groups using an analysis of variance (ANOVA) and subsequently clarified using two-sample, two-tailed protected t-tests. The association between ϵ4 gene dose and annualized whole brain atrophy rates may be characterized using linear tendency ANOVA.

In one embodiment, a flow diagram of the iterative principal component analysis may be as follows:

Let d1 be the atrophy threshold, such that atrophy occurs in location (xi, yi) if its distance to the major axis is greater than d1 and it is below the major axis. The gain threshold d2 is defined similarly. When the following procedure is implemented, none of the points are considered outliers:

(1) PCA Major Axis Determination: Until the major PCA axis converges or the maximal number of iterations is reached:
Do
Apply PCA:
  Excluding outliers, apply PCA to the rest of (xi, yi) points.
Detect and Label Outliers
  Project (xi, yi) points to the minor (second) axis, perpendicular to the major axis.
  Identify the uppermost and lowermost 10% of points in terms of projection distances from median. (any value between 5% and 10% may generate the same PCA axis).
Label these points as outliers.
End Do
(2) Atrophy and/or Gain Voxel Detection:
Detect atrophy and/or gain voxels:
Put back the points removed in the IPCA procedure.
  Project all (xi, yi) points to the minor component,
Label points as outliers using d1 and d2 values.
  Label outliers above the major axis to represent tissue gain (relocation).
  Label outliers below the major axis to represent tissue loss.
  Calculate the percentage of net brain volume change as the ratio of difference between tissue loss and gain to the whole brain volume.

In one embodiment of the iterative principal component analysis, xi and yi may be the voxel intensities at brain location i in the baseline MRI1 and coregistered follow-up MRI2, respectively (i=1, . . . , N, where N is the number of brain voxels). Each of the (xi, yi) pairs may be plotted as a point in an x-y coordinate system. Since most of voxels in the two MRIs are expected to correspond to the same kind of brain tissue (gray matter, white matter, or cerebrospinal fluid (CSF) respectively), most of the (xi, yi) points will be scattered around a ray—a straight line (the iterative principal component analysis linearity assumption) with a positive slope. Instances in which this ray does not pass through the origin in the x-y coordinate system (i.e., it does not have a zero intercept) may be referred to as a linear voxel-intensity shift from the baseline MRI to the follow-up image. Whereas most of (xi, yi) points distributed around this line are encompassed within a relatively narrow band, those points that are a sufficient (i.e., threshold) distance away from the line may be considered outliers, reflecting between-scan differences in voxel intensity.

Outliers may reflect between-scan differences in the brain tissue type (e.g., a voxel corresponding to gray matter in MRI1 and CSF in MRI2 in cases of brain atrophy), changes in white matter intensity, or noise. As indicated below, an outlier threshold that optimizes the trade-off between sensitivity and specificity in the detection of small volume changes (i.e., one that permits detection of relatively subtle changes in brain volume while rejecting false signals and noise) may be identified. Whereas outliers above the ray in the x-y coordinate system represent tissue gain, outliers below the ray represent tissue loss.

The iterative principal component analysis automatically characterizes the ray, identifies significant outliers, and computes between-scan changes in brain volume. While the ray may be defined as the major PCA axis—the eigenvector associated with the largest eigenvalue for the 2_2 covariance matrix of multiple (xi, yi) pairs—it is important to determine this ray free from the potentially confounding (i.e., asymmetric) effect of outliers. By applying the principal component analysis to the (xi, yi) points in an iterative manner, the iterative principal component analysis successively removes outliers in determining the major axis direction. Once the ray is determined, outliers can be identified as those that are a sufficiently large projected distance away from the ray. Utilizing a Gaussian probability density function, the projected distance between each (x, y) pair and the ray may be expressed in terms of standard deviations and p values. For instance, an (x, y) pair 3.291 standard deviation away from the ray would correspond to P=0.0005.

The outlier thresholds may be expressed in terms of terms of P values. For instance, an "outlier threshold" of P=0.0005 may optimize the trade-off between sensitivity and specificity in detecting significant outliers from the coregistered human MRIs, thus permitting the detection of relatively subtle changes in brain volume while rejecting false signals and noise. Brain volume change may be expressed, as is conventional, as I %=((Na_Ng)/N) 100%, where Na and Ng are the number of voxels reflecting significant atrophy or gain, respectively, using a specified outlier threshold, and N is the total number of brain voxels. In the assessment of brain atrophy, the volume change index accounts for any tissue volume gain due to either image-misregistration (which is minimal as the coregistration accuracy is up to within a fraction of a millimeter or localized displacement of brain tissue.

In on embodiment, spatial parametric mapping software may be incorporated into the iterative principal component analysis software to automatically coregister the follow-up MRI to the baseline image (with or without three additional scaling procedures to account for a between-scan drift in voxel geometry (i.e., a between-image change in voxel dimensions that may occur due to gradient calibration drift or variable local field distortions; correct them for image inhomogeneities, and provide baseline measurements of whole-brain or intracranial volume (to compute changes in brain volume as a percentage of baseline measurements). The entire procedure permits researchers to blindly review the images and provide online commenting at the beginning and end of each step as needed.

In another embodiment, after receiving volumetric MRI brain imaging measurements, "voxel-based morphometry" (VBM) may be used to create probabilistic brain maps. The probabilistic brain maps may be used to compute regional alterations in gray matter or white matter. Moreover, non-linear warping algorithms may be used to characterize alterations in the size and shape of the hippocampus, multiple brain regions, variations in gyral and sulcal patterns, and reductions in gray matter.

As noted above, the method may include iteratively processing imaging data and calculating rates of changes for subjects in treated and non-treated groups. In one embodiment, the method may further include determining sample sizes and treatment effect sizes of a subsequent study based on the rates of changes calculated as described above.

Amyloid PET

In another embodiment, the magnitude and spatial extent of amyloid plaque deposition in cognitively unimpaired persons at multiple levels of genetic risk for late-onset AD may be detected. Statistical brain maps may be computed based on computation brain mapping algorithms to show the spatial extent and magnitude of amyloid changes and increases in amyloid accumulation.

A cerebral white matter reference ROI may be used to reduce variability present in prior image processing analyses of longitudinal Aβ PET data, improve the sensitivity to detect longitudinal increases in fibrillar Aβ deposition, and improve the power to evaluate Aβ-modifying treatments. In one embodiment, the method may include receiving brain imaging measurements at a computing device from a PET scanner or an intermediate computing device storing the PET data, such as a server. The brain imaging measurements may be associated with a plurality of subjects, each of which may be either cognitively normal, associated with late or early MCI, or associated with early signs of AD.

The brain imaging measurements may have been collected by the PET scanner at a baseline time point and a follow-up time point, such as a 24-month follow up. In on embodiment, the PET scanner may be a florbetapir PET scanner. In addition to being grouped by cognitive state (e.g., normal, MCI, or AD), the subjects may be further grouped into Aβ-positive (Aβ+) and Aβ-negative (Aβ−) sub-groups based on the brain imaging measurements associated with the baseline time point and a cerebral-to-whole cerebellar florbetapir standard-uptake-value ratio (SUVR). In one embodiment, a corresponding threshold of 1.18 may distinguish between end-of-life persons with and without subsequent post-mortem evidence of moderate-to-frequent neuritic plaques. The cognitively normal subjects may further be split into APOE4 carrier and non-carrier subgroups irrespective of their Aβ status.

After receiving the brain imaging measurements at the computing device, the computing device may execute a set of instructions stored in memory that, when executed, aligns each subject's follow-up measurements and baseline measurements. Execution of the instructions may further deform the images into the coordinates of the Montreal Neurological Institute (MNI) template and use template-based regions-of-interest (ROI) to characterize cerebral target ROI and cerebellar, pontine, and cerebral white matter reference ROI measurements from each set of brain imaging measurements. Execution of the instructions may further compute cerebral-to-respective reference region SUVRs. The executable instructions may include elements of statistical parametric mapping, such as SPM8, Freesurfer, or custom MATLAB scripts. In an embodiment, a cerebral white matter ROI may be a collection of voxels in the corpus callosum and centrum semiovale, other than those closest to gray matter or to ventricles. A template-based corpus callosum mask may be created from the WFU-pick atlas toolbox distributed by the Advanced Neuroscience Imaging Research Laboratory at Wake Forest University School of Medicine. A template-based centrum semiovale mask may be characterized using the FreeSurfer package to generate individual MRI-based ROIs in randomly selected cognitively normal subjects, deform the ROIs into MNI coordinates, average them, and include those voxels with a value of at least 0.5 or another suitable value.

For each Aβ+/− and cognitively normal APOE4 carrier and non-carrier group, 24-month declines in three commonly used clinical ratings, including Mini-Mental State Examination (MMSE) score declines, AD Assessment Scale-Cognitive Sub-Scale, 13 Item Version (ADAS-Cog13) rating increases, and Clinical Diagnostic Rating Sum of the Box (CDR-SB) score increases may be characterized. 24-month cerebral-to-cerebellar, pontine, and cerebral white matter SUVR increases may be examined along with differences between respective Aβ+ versus Aβ− or cognitively normal APOE4 versus non-carrier groups. Relationships between 24-month SUVR increases and clinical declines may be characterized using simple Pearson correlation coefficients. P-values may be computed without correction for multiple comparisons.

For each group, the number of research participants per arm needed to detect a 25% Aβ-modifying treatment effect with 80% power and a two-tailed type-I error of 0.05 in a 12-month placebo-controlled randomized clinical trial (RCT) may be estimated. Sample size estimates may be based on the assumption that SUVR increases are linear. In comparing the impact of different reference ROIs, the sample sizes needed to detect a 25% attenuation in further SUVR increases may be estimated, assuming that the treatment could not clear Aβ below baseline SUVRS (an assumption that might makes sense for the evaluation of a β-secretase [BACE] inhibitor). Smaller sample sizes needed to detect a 25% clearance from the baseline level in the treatment group in comparison to the placebo group (an assumption that might make sense for Aβ immunotherapies) may then be characterized.

Combining FDG-PET and Volumetric MRI

The combined use of FDG-PET and volumetric MRI in the study of a candidate treatment has significant advantages. When using an individual brain imaging process (as opposed to multiple processes), there is a small possibility that a drug's effect on a surrogate endpoint might be unrelated to a disease-modifying effect (e.g., an increase in neuronal activity or brain swelling) or that a drug's effect on a surrogate end-point might actually mask its disease-modifying effect (e.g., a contraction in brain size due to a drug's osmotic or perhaps even plaque-clearing effects). In contrast, the combined used of complementary imaging processes provides converging evidence in support of a drug's disease-modifying effects. It also further reduces the small possibility that the drug's effect on an individual surrogate endpoint is unrelated to its effect on disease progression (an advantage in seeking approval for a drug's disease-modifying effect). It also minimizes the chance that a drug effect on one of the surrogate endpoints would mask its disease-modifying effects (an advantage in proof-of-concept studies). Accordingly, embedding multiple imaging processes (e.g., FDG-PET and volumetric MRI) in clinical trials maximizes the chance of validating one or both surrogate endpoints and helps support a trial's role in the efficient discovery of preclinical AD prevention therapies.

The above advantages far outweigh the additional costs, particularly in cases in which the combined imaging processes are widely available (as it the case with FDG-PET and volumetric MRI).

Embodiments of the systems and methods described herein make it possible to apply these imaging processes to the study of cognitively normal APOE ε4 carriers in preclinical AD prevention trials. In order to conduct preclinical AD prevention trials in these subjects, researchers and ethicists may consider two ways to address the risk of providing genetic information to cognitively normal research participants: withholding information from subjects about their genetic risk with their prior informed consent and including persons with and without a genetic risk for AD (as has been done in naturalistic studies); or counseling potential research subjects about the uncertainties and risks involved in receiving information about their genetic status, obtaining their informed consent to receive this information, and then restricting the study to persons at genetic risk for the disorder.

Notably, other brain regions, other image processes, and other longitudinal comparisons may be used to detect abnormalities in MRI measurements of brain volume in cognitively normal persons at genetic risk for AD. For instance, in one embodiment, VBM (with procedures optimized to remove the influence of non-brain tissue) may be used to investigate regional abnormalities in gray matter density in ∈4 homozygotes, ∈4 heterozytotes, and noncarriers.

In one embodiment, after receiving the brain imaging measurements from the MRI device, executing instructions stored in memory of the computing device may apply an automated algorithm that transforms the brain imaging measurements received from the MRI device into coordinates of a standard brain atlas. The images may be corrected for inhomogeneities, segmented for gray matter, and smoothed. Execution of the instructions my further generate a statistical map of significant differences in gray matter intensity. A significance threshold of 0.005, uncorrected for multiple comparisons, may be used for hypothesized regional effects.

In one exemplary instance in which the foregoing method was performed, ∈4 homozygotes were compared with ∈4 noncarriers and shown to have significantly lower gray matter densities in the vicinity of the right posterior cingulate cortex, a right peri-hippocampal region, and the left parahippocampal and lingual gyri. ∈4 heterozygotes were shown to have significantly lower gray matter density in the vicinity of the left parahippocampalgyrus, the anterior cingulate cortex, and the right temporal cortex. Compared to the ∈4 heterozygotes, the ∈4 homozygotes had significantly lower gray matter density in the vicinity of the left parahippocampal and lingual gyri and in bilateral regions of parietal cortex. Lower measurements of gray matter density in the left parietal and left parahippocampal/lingual areas were correlated with poorer memory scores in the aggregate ∈4 carrier group. Thus, using the systems and methods described herein, cognitively normal ∈4 carriers were shown to have abnormally low gray matter density in heteromodal association and paralimbic regions that are preferentially affected early in AD. By making such findings possible (i.e., by providing sufficient power to determine the findings), embodiments of the system and methods contribute to the efficient evaluation of preclinical AD prevention therapies.

As noted above, embodiments of the method may include determining sample sizes and treatment effect sizes of a subsequent study based on the rates of changes calculated as described above. In one instance, for example, the rates of longitudinal changes may be calculated for the GMRg1 decline between 2-year CMRg1 declines in 10 cognitively normal ∈4 heterozygotes and 15 ∈4 non-carriers 50-63 years of age with a reported first-degree family history of probable AD may be calculated. The rates of change may reveal, for instance, that the ∈4 heterozygotes had significant 2-year CMRg1 declines in the vicinity of temporal cortex, posterior cingulate cortex, prefrontal cortex, basal forebrain, parahippocampal/lingual gyri, and thalamus, and that such declines were significantly greater than those in the ∈4 non-carriers. Although smaller in magnitude, significant declines in posterior cingulate cortex, parietal cortex, anterior cingulate cortex, and the caudate nucleus may be found in the group of ∈4 noncarriers, which could be viewed as physiological markers of normal aging in this age group.

Based on those findings, the number of cognitively normal ∈4 heterozygotes 50-63 years of age per active and placebo treatment group needed to detect an attenuation in these CMRg1 declines in 1 or 2 years may be estimated. In an exemplary study based on such estimates (a 2-year follow-up study performed in 94 of our 47-68 year-old subjects, including 27 ∈4 homozygotes, 27 ∈4 heterozygotes, and 40 ∈4 noncarriers, the ∈4 noncarriers had only modest CMRg1 declines, while the ∈4 carriers had significant CMRg1 declines in the vicinity of temporal, posterior cingulate, and prefrontal cortex, basal forebrain, and the thalamus. The CMRg1 declines in the temporal and prefrontal cortex in the ∈4 carriers were significantly greater than those in the ∈4 noncarriers and were significantly correlated with ∈4 gene dose. These studies suggest that PET devices may be used in connection with the systems and methods described herein to test the potential efficacy of preclinical AD prevention therapies without having to study thousands of research participants, restrict the study to elderly participants, or wait many years to determine whether or when they develop symptoms.

As discussed above, embodiments of the method may include the execution of instructions stored in memory of the computing device that, when executed, perform a fully automated analysis of sequential MRI's using IPCA in independent analyses. Such embodiments may be used to characterize rates of change, such as 2-year rates of whole brain atrophy where the imaging device is an MRI device.

In embodiments, brain imaging measurements may be received at the computing device from more than one imaging device (e.g., from both an FDG-PET scanner and a volumetric MRI machine). In an exemplary study, PET and MRI may both be utilized to late middle-aged ∈4 homozygotes, heterozygotes, and noncarriers and to characterize and contrast the trajectory of decline in brain function and structure in cognitively normal persons at differential risk for AD.

The following is a taxonomy for demonstrating one embodiment of the method, including an illustrative set of test conditions:

1.a. A short term decline (for instance, over a period of 6 months to a year) in structural or functional brain imaging results in persons affected by AD predicts further decline in those individuals. That is, not a single baseline measurement, but the measurement in the changes of brain function or structure over a short-term period of time predicts ultimate clinical decline.

1.b. A short term decline in brain imaging measurements in patients with MCI predicts a higher rate of conversion of those patients to AD. These markers of disease progression predict subsequent clinical outcome.

1.c. A two-year decline in imaging measurements in APOE ∈4 carriers predicts subsequent clinical decline in MCI and AD.

2.a. Once a candidate disease-slowing treatment has been identified and administered to test subjects, then slowing the short term decline predicts subsequent clinical improvement in AD. Likewise, slowing the short term decline in MCI predicts subsequent rate of conversion to AD.

2.b. If the short term brain changes in AD or MCI-affected patients (or in APOE ∈4 carriers) predicts subsequent clinical decline, then a disease slowing treatment in AD and MCI predicts subsequent clinical outcome.

As a result, one embodiment of the method provides that sequential longitudinal declines in brain imaging measurements predict subsequent cognitive decline and increased rates of conversion to MCI and probable AD. Likewise, a putative treatment administered to study participants that slows the declines of brain imaging measurements predicts an improved clinical outcome, such as reduced or delayed conversion to MCI or AD.

Accordingly, the methods and systems described herein provide make prevention studies feasible. Through longitudinal brain imaging studies via FDG-PET, volumetric MRI measurement, or a combination of two or more brain imaging data sets processed through an approach such as Partial Least Squares (PLS) analysis, the aforementioned methods and systems allow for the evaluation of a surrogate marker ultimately a prospective treatment designed to prevent or delay the onset of diseases such as MCI or AD (in addition to the evaluation of treatments designed to reduce the effects of aging on the brain in cognitively normal individuals). The efficacy of preclinical AD may be evaluated through sequential imaging surrogate markers.

The surrogate markers identified above are not limited to FDG PET, volumetric MRI, or combination studies. In some embodiments, longitudinal amyloid imaging measurements or other surrogate markers may be used to predict whether a treatment modality will be effective in delaying or preventing the onset of a brain disorder such as MCI or AD. Through administration of an imaging agent or dye such as Pittsburgh Compound B combined with imaging via techniques such as PET, time-sequenced imaging studies of the brain produce data indicating rates of plaque accumulation/deposition that may be further used to predict a the likelihood of conversion to MCI or AD in a cognitively normal person at risk for AD. Amyloid imaging of treated patients may be monitored over an interval of time, such as six months to a year. If such treated patients show a decline in the rate of plaque deposition, for instance, the putative treatment will be evaluated as positively affecting the clinical progression of AD or MCI.

The methods and systems described herein apply to other risk factors for AD aside from those expressly described for illustrative purposes. For instance, certain embodiments may show that a putative treatment slows the decline in structural or functional brain measurements in cognitively normal persons who are APOE4 non-carriers but that also have higher cholesterol levels. Alternatively, the risk factor may be another susceptibility gene other than the APOE gene.

Linking Functional and Structural Brain Images

As noted above, in some embodiments, brain imaging measurements may be received at the computing device from more than one imaging device (e.g., from both an FDG-PET scanner and a volumetric MRI machine). Partial least squares linkage between the patterns of reductions of gray matter in MRI and the patterns in glucose metabolism in FGG-PET, for instance, provides greater power when testing any change through the combined imaging from two different modalities (e.g., structural via MRI and functional via FDG PET).

Using Partial Least Squares (PLS) as one of a set of possible multivariate network analysis tools, embodiments may utilize the relation between two (or more) image modalities (i.e., inter-modality) to enhance the ability to detect time-related (see FIG. 1 concerning old versus young subjects, for example) or drug-related effects on the brain by examining the regional covariance between functional and structural neuroimaging datasets.

Linearly combining variables in each of the two datasets to form a new variable (representing all variables in that dataset), PLS can identify newly formed variable pairs (latent variable pair), one from each dataset, that has maximal covariance. More generally, PLS can identify a series of paired latent variables such that the covariance of the kth pair is the kth largest among all possible pairs between the two datasets. Note that PLS maximizes covariance, not the correlation coefficient.

To perform this computationally intensive multivariate analysis, submatrix operations may be used to make the computation of high dimensional datasets with covariance analysis using multivariate methods, such as PLS, feasible.

In one embodiment, after receiving the brain imaging measurements at the computing device (from both FDG-PET and MRI imaging devices, for example), the method may include executing instructions stored in memory that, when executed by a processor of the computing device, perform various image pre-processing steps. In an embodiment, the pre-processing steps may be performed by an integrated off-the-shelf software package such as SPM99 made available by the Wellcome Department of Cognitive Neurology in London.

Concerning the brain imaging data received from the MRI device, execution of the instructions may further optimize image segmentation and spatial normalization by discounting the effects of non-brain tissue when generating gray tissue probability maps in coordinates of a Montreal Neurological Institute [MNI] brain template. Execution of the instructions may resample the MRI gray tissue maps into a matrix of voxels (e.g., 26 slices each is a 65×87 matrix of 2×2×4 mm voxels). A common mask may be generated such that voxels in the mask have 20% or higher gray matter concentration (or some other predetermined threshold) for all subjects. Execution of the instructions may further transform the brain imaging measurements received from the PET device into the MNI coordinates using the same image dimensions and the common mask created above. Execution of the instructions may then smooth the resulting MRI and FDG-PET images to final compatible resolutions.

After pre-processing individual images, the resulting PET and MRI data matrix, X and Y (respectively), may be formed. In such cases, X and Y all have n rows—one for each subject. The $i$th row of the matrix X (Y) represents the 3D MRI (PET) data for subject i in the form of a row vector; and jth column consists the data from voxel j. Execution of the instructions may statistically remove global mean PET/MRI measurements on a voxel basis using analysis of covariance. X and Y may be standardized such that mean=0 and STD=1.

In an embodiment, the square root of the largest eigenvalue of the matrix $\Omega=[X'YY'X]$ may correspond to the largest covariance among all possible latent variable pairs between X and Y. The latent variable t of X may be expressed as $t=\Sigma w_i x_i$ where $(w1\ w2\ \ldots\ w.\text{sub.kx})'$ is the column eigenvector of $\Omega$, and x is the $i^{th}$ column of X. The corresponding latent variable u of Y may be formed similarly. The second largest covariance may be obtained by first regressing t out of X and u out of Y, and then repeating the above procedure using the residual matrices. The same iteration procedure also works for the $3^{rd}$ largest covariance etc.

Subsequent statistical analysis of the PLS results (the latent variable pair—its value for each subject is referred to as subject scores below—and the associated covariance) is an important part of the PLS analysis and requires dedicated tools such as non-parametric permutation tests. In one embodiment, the subject score pair may be examined by linear regression and used to check their power to distinguish the young adult group from the older group. The latent variables may then be mapped back to MRI space (singular images) for visual inspection.

Because the resulting data matrix is extremely large, reading it into memory of the computing device in its entirety is not practical and therefore constitutes a significant technical problem. Thus, to make the computation possible for a high-dimensional data matrix, embodiments of the method include a step of resampling the imaging data. Resampling the imaging data may include resampling with a second voxel size larger than first voxel size. By increasing the size of each voxel, the overall number of voxels may be reduced.

The method may further include partitioning the data matrix into a plurality of sub-matrices and reading the sub-matrices into memory of the computing device one at a time at a rate determined by when the processor of the computing device requires each sub-matrix to iteratively process the imaging data stored in the data matrix. In some embodiments, the results may be saved as sub-matrices and only matrix operations that can act separately on sub-matrices and result in a sub-matrix form may be used. In such cases, the only operations in each iteration are matrix-by-vector/scalar multiplications.

Iteratively processing the imaging data may include calculating a rate of change for the subjects in the treated group either during or following treatment with the prospective AD treatment at issue over a predetermined period of time. Iteratively processing the imaging data may include calculating a rate of change for the subjects in the untreated group over substantially the same predetermined period of time.

In one exemplary study performed using the foregoing methods, PLS was used to investigate the regional covariance between functional and structural brain imaging data from cognitively normal 15 younger (31.3.+−0.4.8 years old) and 14 older (70.7.+−0.3.5 years old) volunteers. FDG-PET and volumetric $T_1$-weighted MRI data were acquired in each subject with his/her informed consent, and under guidelines approved by human-subjects committees at Good Samaritan Medical Center and the Mayo Clinic. PET was performed with the 951/31 ECAT scanner produced by Siemens of Knoxville, Tenn. as the subjects, who had fasted for at least 4 hours, lay quietly in a darkened room with their eyes closed and directed forward. MRI data was acquired using a 1.5 T Signa system produced by General Electric of Milwaukee, Wis.) and $T_1$-weighted, 3D pulse sequence (radio-frequency-spoiled gradient recall acquisition) in the steady state. The pooled data from the younger and older subjects was analyzed by PLS without reference to the group age difference.

For the datasets used in this application, the computation of the first singular image pair took approximately 96 hours for a covariance matrix of 45,666 by 45,666. The PLS algorithm was implemented in MATLAB (MathWorks, MA) on an XP1000 Alpha station.

The PET and MRI subject scores were closely correlated (R=0.84, p<7.2e-09). As indicated in FIG. 1, there was no overlap between the younger (diamonds) and older subjects (circles) using the combination of PET and MRI scores and, indeed, the combination of scores maximized the group separation.

As shown in FIG. 2, the first singular PET (left) and MRI images are shown. Reduced cerebral metabolic rate for glucose (CMRgl) and gray matter concentration were each observed in the vicinity of medial frontal, anterior cingulate, bilateral superior frontal and precuneus cortex. Lower CMRgl was observed in the absence of lower gray matter concentration in the vicinity of the posterior cingulate and bilateral inferior frontal cortex; and measurements of CMRgl and gray matter concentration were each relatively preserved in the vicinity of occipital cortex and the caudate nucleus. Analyzing the paired PET and MRI images from normal older and younger adults, the exemplary PLS method revealed a regional pattern of association between brain function and brain structure that differed as a function of normal aging.

In a preliminary cross-sectional study, the regional covariance or linkage between cerebral metabolic and gray matter patterns that best accounted for differences in brain function and structure related to normal aging were characterized. Embodiments of the PLS-related method facilitate the investigation of relationships between brain function and brain structure, providing increased power in the diagnosis, early detection, and tracking of disease-related brain changes and providing increased power in the evaluation of a candidate treatments' disease-modifying effects.

For real persons at risk for Alzheimer's disease, a neurodegenerative disease, or brain aging, a measurement's rate of change can be characterized during or following the real persons' treatment with disease-preventing or neurological age-slowing therapy. For hypothetical persons similar to the real persons at risk for these conditions but who are not so treated, the measurement's rate of change can be characterized over a like time interval. The disease-preventing or age-slowing therapy's efficacy is suggested by a smaller measurement rate of change over the like time interval in the real persons treated than in the hypothetical persons not so treated, even in the absence of clinical decline over the time interval. Measurements of neurodegenerative disease progression will have significantly higher rates of change in persons clinically affected by or at risk for the disease than in those persons at lower risk for the neurodegenerative disease.

The treatment being evaluated may be putative AD prevention therapy, putative neurodegenerative disease prevention therapy, a putative therapy to slow an aspect of brain aging, or a combination of the foregoing. These therapies, and methods for their evaluation, are discussed below.

Evaluation of an AD Prevention Therapy

To evaluate an AD prevention therapy, one or more measurements are taken in real persons (i.e., human subjects) at two or more different times each of which is found in the absence of treatment to be associated with statistically significant (i) rates of change in AD patients, or (ii) greater rates of change in MCI patients who subsequently show further cognitive decline than in MCI patients who do not, or (iii) greater rates of change in persons thought to be at higher AD risk that are cognitively normal or not disabled by AD than persons thought to be at lower AD risk that are cognitively normal or not disabled by AD.

Figure 5:
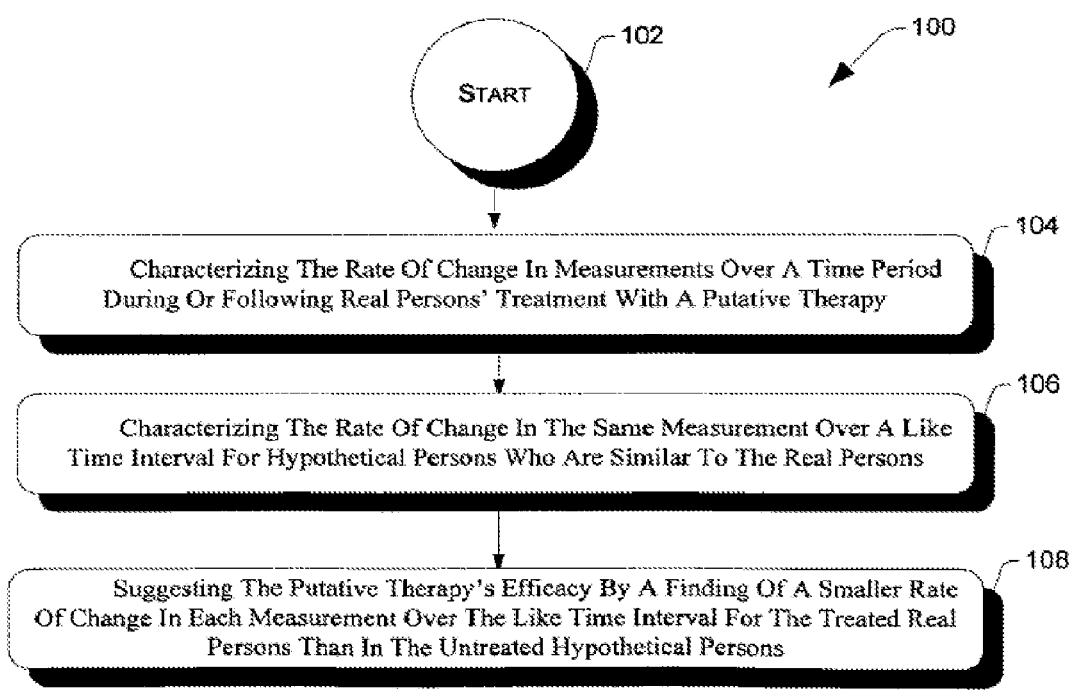
FIG. 5 shows a method of evaluating the efficacy of a therapy for Alzheimer's Disease.

Embodiments of the method may include using the measurements with respect to real persons who have an AD risk factor but do not have clinically significant cognitive impairment. As shown in FIG. 5, a method 100 may begin at step 102 and include a step 104 of determining the rate of change in each measurement over a time period during or following the real persons' treatment with a putative AD prevention therapy.

For hypothetical persons who are similar to the real persons in their risk for AD, age, and absence of clinically significant cognitive impairment but who are not treated with the putative AD prevention therapy, the method 100 may include a step 106 of determining the rate of change in the same measurement over a like time interval.

Based on the foregoing, the efficacy of the putative AD prevention therapy may, at step 108, be estimated by a finding of a statistically smaller rate of change in each measurement over the like time interval for the real persons treated with the putative AD prevention therapy than in the hypothetical persons that are not treated with the putative AD prevention therapy.

Each of the measurements can be a brain imaging measurement, an electrophysiological measurement, a biochemical measurement, a molecular measurement, a transcriptomic measurement, a proteomic measurement, a cognitive measurement, a behavior measurement, or a combination of the foregoing. In one embodiment, the measurements can be the cerebral metabolic rate for glucose (CMRg1) in brain regions found to have a greater rate of CMRg1 decline in cognitively normal persons at higher risk for AD than in those with a lower risk. As discussed above, CMRg1 may be measured using FDG-PET. The real and hypothetical subjects may have at least one copy of the APOE ϵ4 allele.

Each measurement may be the rate of change in brain tissue volume or the rate of change in cerebrospinal fluid volume so as to provide information about the rate of brain atrophy. The brain tissue volume or the cerebrospinal fluid volume may be measured using magnetic resonance imaging (MRI). In such cases, the real and hypothetical persons will preferably have at least one copy of the APOE ϵ4 allele.

In one embodiment, each of the measurements may provide an indirect assessment of the progression of AD pathology, where the AD pathology may be the loss of intact neurons or synapses, the formation of amyliod plaques, the formation of neurofibrillary tangles, or a combination of the foregoing.

Figure 6:
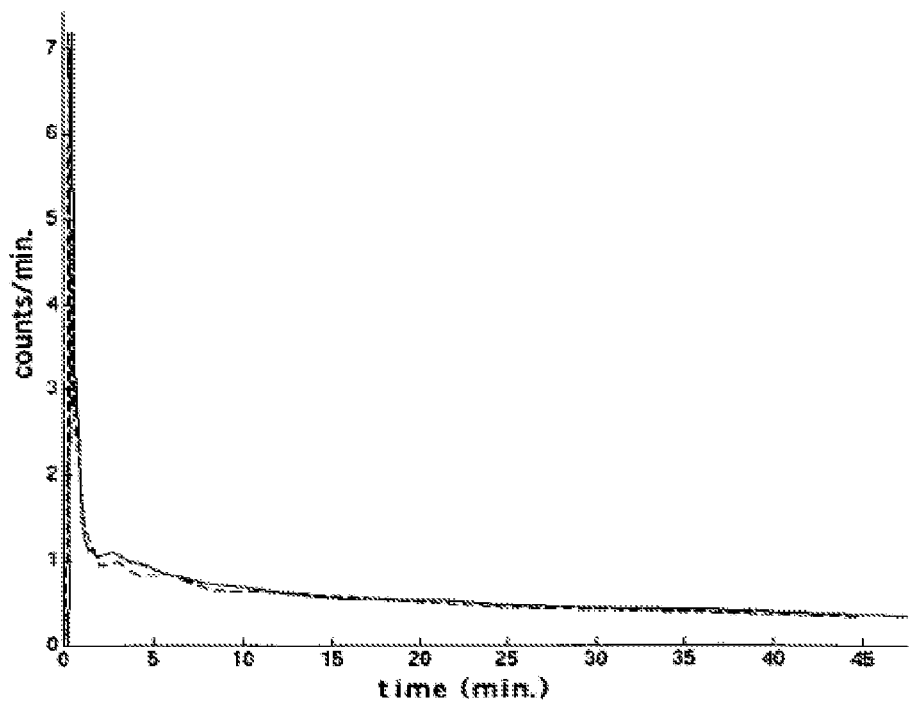
FIG. 6 illustrates a time-activity curve derived from a blood sample compared to a time-activity curve derived from a brain image.

Each measurement received at the computing device may be a concentration of amyloid proteins, a concentration of amyloid oligomers, a concentration of amyloid plaques, a concentration of tau, a concentration of phosphorylated tau proteins, a concentration of tangles, a concentration of F2-isoprostanes, a concentration of lipid peroxidation, a concentration of inflammatory, activated microglial, a molecular immune change, and a molecular change associated with the progression of AD. Each measurement may be a reflection of the activity or integrity of brain cells, a reflection of the activity or integrity of white matter tracks, or a combination of the foregoing. Each measurement may be a neurotransmitter characteristic, a neuroreceptor characteristic, a neurochemical characteristic, a molecular characteristic, a physiological characteristic, or a combination of the foregoing. Each measurement can be made by a brain imaging technique, a biological assay, and combination of the foregoing. As illustrated in FIG. 6, the biological assay may be performed using a sample that is a body fluid, cerebrospinal fluid, blood (e.g., as shown in FIG. 6), saliva, urine, a body tissuee.

The brain imaging technique may include various PET and single photon emission tomography radiotracer methods, a structural, functional, perfusion-weighted, or diffusion-weighted MRI, x-ray computed tomography, magnetic resonance spectroscopy measurements of N-acetyl aspartic acid, myoinositol, and other chemical compounds, electroencephalography, quantitative electroencephalography, event-related potentials, other electrophysiological procedures, magnetoencephalography, an electrophysiological method, or a combination of the foregoing.

The AD risk factor may be a genetic risk factor, a non-genetic risk factor, or a combination of the foregoing. The genetic risk factor may be the presence of one or two copies of the APOE E4 allele, the presence of other confirmed susceptibility genes, the presence of a presenilin 1 mutation, presenilin 2 mutation, amyloid precursor protein mutation, or other mutations or gene shown to cause AD, an aggregate genetic risk score that is based upon a person's number of susceptibility genes and their individual contribution to an AD risk, a family history of AD, or a combination of the foregoing.

The non-genetic risk factor may be head trauma associated with loss of consciousness, a higher than normal cholesterol level, a higher than normal homocysteine level, a brain imaging measurement thought to be associated with a higher than normal risk of subsequent cognitive decline, MCI, or AD, being at least 60 years of age, a biological marker associated with a higher that normal risk of subsequent cognitive decline, MCI, or AD, a cognitive measurement thought to be associated with a higher than normal risk of subsequent cognitive decline, MCI, or AD, a behavioral measurement thought to be associated with a higher than normal risk of subsequent cognitive decline, MCI, or AD, or a combination of the foregoing.

The validity of each measurement as a "therapeutic surrogate" will preferably be further supported to suggest the efficacy of the putative AD prevention therapy by a statistically significant relationship between rates of change in each measurement over the like time interval and subsequent clinical decline in patients with AD or MCI or in cognitively normal or non-disabled persons at AD risk. Further, the validity of each measurement as a "therapeutic surrogate" will preferably be further supported to suggest the efficacy of the putative AD prevention therapy by a statistically significant showing of how the ability of the putative AD prevention therapy to slow the rate of change in each said measurement over the like time interval is associated with slower rates of subsequent clinical decline in patients with AD or MCI or in cognitively normal or non-disabled persons at AD risk.

The putative AD prevention therapy may be a pharmacological prescription, an over-the-counter medication, an immunization therapy, a biological therapeutic, a dietary supplement, a dietary change, a physical exercise, a mental exercise, a lifestyle change intended to promote healthy living, decrease the risk of cognitive decline, MCI, AD, or cardiovascular disease, or a combination of the foregoing. The putative therapy may be applied to a patient who has AD, MCI, or is a cognitively normal or non-disabled person who has an AD risk factor.

Prospective treatments for neurodegenerative diseases may be evaluated. In one embodiment, the neurodegenerative disease may be Alzheimer's disease, Dementia with Lewy Bodies, Parkinson's disease, Parkinson's dementia, a frontotemporal dementia, a tauopathy, other progressive dementias, amyotropic lateral sclerosis, other progressive neuromuscular disorders, multiple sclerosis, other progressive neuroimmunological disorders, Huntington's disease, a focal or generalized brain disorder which involves a progressive loss of brain function over time, or a combination of the foregoing.

In such cases, the measurements received at the computing device may be a brain imaging measurement, an electrophysiological measurement, a biochemical measurement, a molecular measurement, a transcriptomic measurement, a proteomic measurement, a cognitive measurement, a behavior measurement, or a combination of the foregoing.

One of the measurements may be the cerebral metabolic rate for glucose (CMRg1) in brain regions found to have a greater rate of CMRg1 decline in patients with Parkinson's disease patients who subsequently development Parkinson's dementia than in Parkinson's patients who do not subsequently develop Parkinson's dementia. Here, the CMRg1 is measured using fluorodeoxyglucose (FDG) positron emission tomography (PET). The real and hypothetical persons may each have Parkinson's disease but may not have dementia at the beginning of the like time interval.

Each of the measurements may be a brain imaging measurement, an electrophysiological measurement, or a combination of the foregoing. Each measurement may be a biochemical assay, a molecular assay, or a combination of the foregoing. In one implementation, at least one of the measurements will preferably have a greater rate of change in persons at a higher risk for the neurodegeneragive disease that in persons at a lower risk for the neurodegeneragive disease in the absence of disabling symptoms of the neurodegeneragive disease.

The validity of each measurement as a "therapeutic surrogate" will preferably be further supported to suggest the efficacy of the putative neurodegenerative disease prevention therapy by a statistically significant relationship between rates of change in each said measurement over the like time interval and subsequent clinical decline in patients affected by or at risk for the neurodegenerative disease. Moreover, the validity of each measurement as a "therapeutic surrogate" will further be supported to suggest the efficacy of the putative neurodegenerative disease prevention therapy by a statistically significant showing of how the ability of the putative neurodegenerative disease prevention therapy to slow the rate of change in each said measurement over the like time interval is associated with slower rates of subsequent clinical decline in patients affected by or at risk for the neurodegenerative disease.

The putative neurodegenerative disease prevention therapy may be a pharmacological prescription, an over-the-counter medication, an immunization therapy, a biological therapeutic, a dietary supplement, a dietary change, a physical exercise, a mental exercise, a lifestyle change intended to promote healthy living, reduced the risk of the neurodegenerative disorder or its symptoms, or reduce the risk of cardiovasculare disease, or a combination of the foregoing. The person being treated with the neurodegenerative disease prevention therapy can have a neurodegenerative disease or may be a person without disabling symptoms of a neurodegenerative disease who has a neurodegenerative disease risk factor.

The foregoing steps may likewise be applied to evaluate a putative therapy to slow the progressive effects of aging on the brain. To evaluate a putative therapy to slow an aspect of brain aging, one or more measurements may be taken in real persons at two or more different times. The measurements may be found in the absence of treatment to be associated with statistically significant rates of change associated with aging in patients who do not have clinical signs or symptoms of a progressive brain disorder. "Normal aging" may be characterized by the absence of a brain disorder of the absence of a medical problem that could affect the brain. "Healthy aging" may be further characterized by the absence of any signs or symptoms of an age-related brain disorder. "Very health aging" may be further characterized by the absence of one or more known risk factors for an age-related disorder. For instance, a risk factor can be having a copy of the APOE $\epsilon$4 allele.

In connection with the foregoing, a system for evaluating a prospective treatment for Alzheimer's disease (AD) may include an imaging device that takes a plurality of brain imaging measurements from each of a plurality of human subjects. The brain imaging measurements may measure a surrogate marker found in the absence of treatment to be correlated with a clinical severity of AD symptoms. The measurements may be arranged in a data matrix and may be associated with a first voxel size.

Each subject may be one of a homozygote of alleles associated with AD, a heterozygote of alleles associated with AD and mild cognitive impairment (MCI), and a non-carrier of alleles associated with AD who has no clinical symptoms of AD. In on embodiment, the alleles may be $\epsilon$3/$\epsilon$4 alleles of the APOE gene known to influence the probability of a subject developing AD.

The system may further include a computing device having a processor and memory storing executable instructions. The computing device may be communicatively coupled to the imaging device and may receive the brain imaging measurements from the imaging device. The computing device may also receive subject data concerning each of the subjects. The subject data may include an age range, risk of Alzheimer's disease (AD), the presence or absence of clinical symptoms of AD, the plurality of human subjects divided based on the subject data into a first group of subjects treated with a prospective AD treatment of interest and a second group of subjects not treated with the prospective AD treatment.

After receiving the subject data, the computing device may store the subject data concerning each of the subjects in memory of the computing device. The computing device may include executable instructions stored in the memory of the computing device that, when executed by the processor of the computing device, transform the brain imaging measurements into a voxel-based data matrix, resample the brain imaging measurements with a second voxel size larger than the first voxel size to reduce a number of voxels of the measurements. Execution of the instructions may further partition the data matrix into a plurality of sub-matrices and read the sub-matrices into memory of the computing device one at a time at a rate necessary to iteratively calculates a rate of change for the treated group of subjects during or following treatment with the AD therapy. The calculated rate of change may be based on the measurements for each person in the treated group over a predetermined time interval. A rate of change for the untreated group of subjects may likewise be iteratively calculated based on the sub-matrices of the brain imaging measurements.

Through further execution of the instructions, the computing device may then compare the rate of change calculated for the treated group to the rate of change calculated for the untreated group and determine whether a difference between the rate of change calculated for the treated group and the rate of change calculated for the untreated group is statistically significant. The difference may be deemed statistically significant by comparison to a predetermined statistical threshold. As discussed above, the rate of change and the determination regarding statistical significance may indicate an efficacy of the AD therapy and a validity of the surrogate marker.

Embodiments of the systems and methods described herein may be implemented in a network environment that may include a communication network, one or more user devices, measurement devices, databases, and servers. Devices in such a network environment may communicate with each other via the communications network.

The communication network may be a local, proprietary network (e.g., an intranet) and/or may be a part of a larger wide-area network. The communications network may include a local area network (LAN), which may be communicatively coupled to a wide area network (WAN) such as the Internet. The Internet is a broad network of interconnected computers and servers allowing for the transmission and exchange of Internet Protocol (IP) data between users connected through a network service provider. Examples of network service providers are the public switched telephone network, a cable service provider, a provider of digital subscriber line (DSL) services, or a satellite service provider. Such a communications network allows for communication between the various components of the network environment.

Users may use any number of different electronic user devices, such as general purpose computers, mobile phones, smartphones, personal digital assistants (PDAs), portable computing devices (e.g., laptop, netbook, tablets), desktop computing devices, handheld computing device, or any other type of computing device capable of communicating over communication network. User devices may also be configured to access data from other storage media, such as memory cards or disk drives as may be appropriate in the case of downloaded services. User device may include standard hardware computing components such as network and media interfaces, non-transitory computer-readable storage (memory), and processors for executing instructions that may be stored in memory. Such user devices may be used to enter and communicate information from various locations to service providers, databases, and/or other servers.

Service provider may include any type of server or other computing device as is known in the art, including standard hardware computing components such as network and media interfaces, non-transitory computer-readable storage (memory), and processors for executing instructions or accessing information that may be stored in memory. The functionalities of multiple servers may be integrated into a single server. Any of the aforementioned servers (or an integrated server) may take on certain client-side, cache, or proxy server characteristics. These characteristics may depend on the particular network placement of the server or certain configurations of the server.

A server may be associated with a particular medical practice or research facility and located in the same local network as user devices. Alternatively, the server may be located remotely (e.g., in the cloud) and may be associated with a third party that provides services in accordance with embodiments of the present invention. In some instances, the services may be provided via software (e.g., software as a service) downloaded from server to one or more user devices. Updated software may similarly be downloaded as the updates become available or as needed.

The server may further be associated with or have access to one or more databases storing the electronic medical records. Similar to the server, such a database may be local or located remotely from the particular medical practice, research facility, or other location where information is obtained regarding patients and/or study subjects whose electronic records are being stored. As noted above, medical practitioners, researchers, or other evaluation participants may use any number of user devices to enter current information regarding a patient/study subject and update the associated electronic record. For example, nurses may periodically measure a patient's vital signs and observe other symptoms. Such measurements, observations, and other types of updates to the electronic record may then be sent and stored in the databases where the server may monitor the electronic records stored in the database(s) and evaluate such records (and their updates). Such information may be analyzed in light of certain predefined rules. Such rules may be defined sets of indicators that are indicative of neurodegenerative decline. The sets of indicators may include any variety of conditions discussed herein. Such conditions may be selected by an evaluator based on the particular therapy being evaluated.

The methods described herein may be embodied as executable instructions in a non-transitory computer readable storage medium including but not limited to a CD, DVD, or non-volatile memory such as a hard drive. The instructions of the storage medium may be executed by a processor (or processors) to cause various hardware components of a computing device hosting or otherwise accessing the storage medium to effectuate the method. The steps identified herein (and the order thereof) are exemplary and may include various alternatives, equivalents, or derivations thereof including but not limited to the order of execution of the same.

The present invention may be implemented in an application that may be operable using a variety of devices. Non-transitory computer-readable storage media refer to any medium or media that participate in providing instructions to a central processing unit (CPU) for execution. Such media can take many forms, including, but not limited to, non-volatile and volatile media such as optical or magnetic disks and dynamic memory, respectively. Common forms of non-transitory computer-readable media include, for example, a floppy disk, a flexible disk, a hard disk, magnetic tape, any other magnetic medium, a CD-ROM disk, digital video disk (DVD), any other optical medium, RAM, PROM, EPROM, a FLASHEPROM, and any other memory chip or cartridge.

Various forms of transmission media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU. Various forms of storage may likewise be implemented as well as the necessary network interfaces and network topologies to implement the same.

While preferred embodiments of this invention have been shown and described, modifications thereof can be made by one skilled in the art without departing from the spirit or teaching of this invention. The embodiments described herein are exemplary only and are not limiting. Many variations and modifications of the method and any apparatus are possible and are within the scope of the invention. One of ordinary skill in the art will recognize that the process just described may easily have steps added, taken away, or modified without departing from the principles of the present invention. Accordingly, the scope of protection is not limited to the embodiments described herein, but is only limited by the claims that follow, the scope of which shall include all equivalents of the subject matter of the claims.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the invention as defined by the appended claims and otherwise appreciated by one of ordinary skill in the art. The scope of the invention should, therefore, be determined not with reference to the above description, but instead should be determined with reference to the appended claims along with their full scope of equivalents.

What is claimed is:

1. A method for determining the efficacy of a prospective prevention therapy for Alzheimer's disease (AD) in persons having no clinical symptoms of AD, the method comprising:

receiving at a computing device a plurality of brain imaging measurements from one or more positron emission tomography (PET) scanners, the brain imaging measurements indicating a concentration of amyloid plaques or neurofibrillary tangles deposited in a brain of each of a plurality of subjects in an AD prevention therapy study, each subject having no clinical symptoms of AD and at least one of Down syndrome or a concentration of amyloid plaques or neurofibrillary tangles deposited in the brain, wherein the concentration is at least equal to a threshold concentration of amyloid plaques or neurofibrillary tangles deposited in the brain, and wherein a first portion of the measurements were obtained by the PET scanner from a first group of the subjects who first received a prospective prevention therapy for AD, a second portion of the measurements were obtained by the PET scanner from a second group of the subjects who did not first receive the prospective prevention therapy for AD; and executing instructions stored in memory of the computing device, wherein execution of the instructions by a processor of the computing device:
  determines a correlation between the brain imaging measurements and a plurality of coordinates of a brain atlas,
  extracts from the brain imaging measurements data corresponding to a region of interest identified by at least a portion of the brain atlas coordinates, the data indicating the concentration of amyloid plaques or neurofibrillary tangles deposited in the region of interest,
  calculates based on a predetermined interval a rate of change in the concentration of amyloid plaques or neurofibrillary tangles deposited in the region of interest for each of the plurality of subjects,
  compares the rates of change in the concentration of amyloid plaques or neurofibrillary tangles deposited in the region of interest calculated for the first group of the subjects to the rates of change in the concentration of amyloid plaques or neurofibrillary tangles deposited in the region of interest calculated for the second group of the subjects,
  determines that a difference between the rates of change in the concentration of amyloid plaques or neurofibrillary tangles deposited in the region of interest between the first group of the subjects and the second group of the subjects is statistically significant, and
  reports to a user of the computing device by way of a user interface that based on the statistically significant difference the prospective prevention therapy for AD is efficacious in persons having no clinical symptoms of AD and at least one of Down syndrome or at least the threshold concentration of amyloid plaques or neurofibrillary tangles deposited in the brain.

2. The method of claim 1, further comprising receiving at the computing device a second plurality of brain imaging measurements from a magnetic resonance imaging (MRI) machine, the MRI brain imaging measurements indicating a brain tissue volume associated with each subject.

3. The method of claim 1, further comprising receiving at the computing device a plurality of subject data, wherein the subject data includes an age range and a level of risk of developing AD.

4. The method of claim 1, wherein each subject has Down syndrome and a concentration of amyloid plaques or neurofibrillary tangles deposited in the brain, wherein the concentration is at least equal to the threshold concentration of amyloid plaques or neurofibrillary tangles deposited in the brain.

5. A method for determining the efficacy of a prospective prevention therapy for Alzheimer's disease (AD) in persons having no clinical symptoms of AD, the method comprising:
  receiving at a computing device subject data concerning each of a plurality of subjects in an AD prevention therapy study, the subject data including an age range and a level of risk of developing AD, the subjects each having no clinical symptoms of AD and at least one of Down syndrome or a concentration of amyloid plaques or neurofibrillary tangles deposited in a brain of each subject, wherein the concentration is at least equal to a threshold concentration of amyloid plaques or neurofibrillary tangles deposited in the brain, and the subjects being divided based on the subject data into a first group of subjects treated with the prospective prevention therapy for AD and a second group of subjects not treated with the prospective prevention therapy for AD;
  storing the subject data concerning each of the subjects in memory of the computing device;
  receiving at the computing device a plurality of brain imaging measurements from one or more positron emission tomography (PET) scanners, the brain imaging measurements indicating a concentration of amyloid plaques or neurofibrillary tangles deposited in the brain of each subject, wherein the concentration of amyloid plaques or neurofibrillary tangles deposited in the brain is a surrogate marker found in the absence of treatment to be correlated with clinical severity of AD symptoms; and
  executing instructions stored in memory of the computing device, wherein execution of the instructions by a processor of the computing device:
    determines a correlation between the brain imaging measurements and a plurality of coordinates of a brain atlas, extracts from the brain imaging measurements data corresponding to a region of interest identified by at least a portion of the brain atlas coordinates, the data indicating the concentration of amyloid plaques or neurofibrillary tangles deposited in the region of interest,
    calculates based on a predetermined interval a rate of change in the concentration of amyloid plaques or neurofibrillary tangles deposited in the region of interest for each of the subjects in the treated group during or following treatment with the prospective prevention therapy for AD and for each of the subjects in the untreated group,
    calculates a difference between the rates of change in the concentrations of amyloid plaques or neurofibrillary tangles deposited in the region of interest calculated for the treated group and the rates of change calculated for the untreated group,
    compares the calculated difference to a predetermined threshold of statistical significance, and
    reports to a user of the computing device by way of a user interface that the prospective prevention therapy for AD is efficacious when the calculated difference between the rates of change in the concentration of amyloid plaques or neurofibrillary tangles deposited in the region of interest for the treated and untreated groups meets or exceeds the predetermined threshold of statistical significance.

6. The method of claim 5, further comprising receiving at the computing device a second plurality of brain imaging measurements from a magnetic resonance imaging (MRI) machine, the MRI brain imaging measurements indicating a brain tissue volume associated with each subject.

7. The method of claim 5, further comprising receiving at the computing device a second plurality of brain imaging measurements from a magnetic resonance imaging (MRI) machine, the MRI brain imaging measurements indicating a cerebrospinal fluid volume associated with each subject.

8. The method of claim 5, further comprising performing a biological assay using a sample selected from the group consisting of: a body fluid, cerebrospinal fluid, blood, saliva, urine, and a body tissue.

9. The method of claim 5, further comprising receiving at the computing device a second plurality of brain imaging measurements from a device configured to perform a procedure selected from the group consisting of:
single photon emission tomography radiotracer;
structural, functional, perfusion-weighted, or diffusion-weighted MRI;
x-ray computed tomography;
magnetic resonance spectroscopy measurements of N-acetyl aspartic acid, myoinositol or another chemical compound associated with the brain;
electroencephalography, quantitative electroencephalography, or event-related potentials; electrophysiological procedures;
magnetoencephalography; and
a combination of the foregoing.

10. The method of claim 5, wherein the level of risk of developing AD is based on a severity level of Down syndrome or the concentration of amyloid plaques or neurofibrillary tangles deposited in the brain.

11. The method of claim 10, wherein the level of risk is further based on a non-genetic risk factor selected from the group consisting of:
a prior head trauma associated with loss of consciousness;
a cholesterol level;
a homocysteine level;
a brain imaging measurement associated with subsequent cognitive decline or mild cognitive impairment (MCI);
being at least 60 years of age;
a biological marker associated with subsequent cognitive decline or MCI;
a cognitive measurement associated with subsequent cognitive decline or MCI; a behavioral measurement associated with subsequent cognitive decline or MCI; and
a combination of the foregoing.

12. The method of claim 5, wherein execution of the instructions by the processor further reports to the user by way of the user interface that the concentration of amyloid plaques or neurofibrillary tangles deposited in the region of interest is a valid surrogate marker for the efficacy of the prospective prevention therapy for AD when the calculated difference between the rates of change in the concentration of amyloid plaques or neurofibrillary tangles deposited in the region of interest for the treated and untreated groups meets or exceeds the predetermined threshold of statistical significance and the difference indicates less clinical increase in the concentration of amyloid plaques or neurofibrillary tangles deposited in the region of interest in subjects of the treated group than in subjects of the untreated group.

13. The method of claim 5, wherein execution of the instructions by the processor further reports to the user by way of the user interface that the concentration of amyloid plaques or neurofibrillary tangles deposited in the region of interest is a valid surrogate marker for the efficacy of the prospective prevention therapy for AD when the calculated difference between the rates of change in the concentration of amyloid plaques or neurofibrillary tangles deposited in the region of interest for the treated and untreated groups meets or exceeds the predetermined threshold of statistical significance and the difference indicates a slower clinical increase in the concentration of amyloid plaques or neurofibrillary tangles deposited in the region of interest in subjects of the treated group than in subjects of the untreated group.

14. The method of claim 5, wherein the prospective prevention therapy for AD is selected from the group consisting of: a pharmacological prescription, an over-the-counter medication, an immunization therapy, a biological therapeutic, a dietary supplement, a dietary change, a physical exercise, a mental exercise, a lifestyle change, and a combination of the foregoing.

15. A system for determining the efficacy of a prospective prevention therapy for Alzheimer's disease (AD) in persons having no clinical symptoms of AD, the system comprising:
at least one positron emission tomography (PET) scanner configured to take a plurality of brain imaging measurements from each of a plurality of subjects in an AD prevention therapy study, each subject having no clinical symptoms of AD and at least one of Down syndrome or a concentration of amyloid plaques or neurofibrillary tangles deposited in a brain of each subject, wherein the concentration is at least equal to a threshold concentration of amyloid plaques or neurofibrillary tangles deposited in the brain, and wherein the brain imaging measurements indicate a concentration of amyloid plaques or neurofibrillary tangles deposited in the brain of each subject and the concentration of amyloid plaques or neurofibrillary tangles deposited in the brain is a surrogate marker found in the absence of the prevention therapy for AD to be correlated with a clinical severity of AD symptoms; and
a computing device having a processor and memory storing executable instructions, wherein the computing device is communicatively coupled to the PET scanner by a communications network and is configured to:
receive the brain imaging measurements from the PET scanner,
receive subject data concerning each of the subjects, the subject data including an age range and a level of risk of developing AD, the subjects divided based on the subject data into a first group of subjects treated with the prospective prevention therapy for AD and a second group of subjects not treated with the prospective prevention therapy for AD,
store the subject data concerning each of the subjects in memory of the computing device, and
execute instructions stored in the memory of the computing device, wherein execution of the instructions by the processor of the computing device:
determines a correlation between the brain imaging measurements and a plurality of coordinates of a brain atlas,
extracts from the brain imaging measurements data corresponding to a region of interest identified by at least a portion of the brain atlas coordinates, the data indicating the concentration of amyloid plaques or neurofibrillary tangles deposited in the region of interest, calculates based on a predetermined interval a rate of change in the concentration of amyloid plaques or neurofibrillary tangles deposited in the region of interest for each of the subjects in the treated group during or following treatment with the prospective prevention therapy for AD and for each of the subjects in the untreated group, calculates a difference between the rates of change in the concentration of amyloid plaques or neurofibrillary tangles deposited in the region of interest calculated for the treated and untreated groups, compares the calculated difference to a predetermined threshold of statistical significance, and reports to a user of the computing device by way of a user interface that the prospective prevention therapy for AD is efficacious when the calculated difference between the rates of change in the concentrations of amyloid plaques or neurofibrillary tangles deposited in the region of interest for the treated and untreated groups meets or exceeds the predetermined threshold of statistical significance.

* * * * *